(12) United States Patent
Kamp et al.

(10) Patent No.: US 7,373,073 B2
(45) Date of Patent: May 13, 2008

(54) PHOTONIC COLLOIDAL CRYSTAL COLUMNS AND THEIR INVERSE STRUCTURES FOR CHROMATOGRAPHY

(75) Inventors: Ulrich Kamp, LM #308, 80 St. George Street, Toronto (CA) M5S 3H6; Vladimir Kitaev, Apt #505, 45 Caroline Street North, Waterloo (CA) N2L 2Y6; Georg von Freymann, Toronto (CA); Geoffrey Alan Ozin, Toronto (CA); Scott Andrew Mabury, Toronto (CA)

(73) Assignees: Ulrich Kamp, Toronto (CA); Vladimir Kitaev, Waterloo (CA); The Governing Council of the University of Toronto, Toronto (CA)

( * ) Notice: Subject to any disclaimer, the term of this patent is extended or adjusted under 35 U.S.C. 154(b) by 267 days.

(21) Appl. No.: 11/005,457

(22) Filed: Dec. 7, 2004

(65) Prior Publication Data
US 2006/0120683 A1  Jun. 8, 2006

(51) Int. Cl.
*G02B 6/00* (2006.01)
(52) U.S. Cl. ............... 385/141; 385/147; 385/140; 385/125
(58) Field of Classification Search ............ 385/122, 385/123, 129, 141, 147, 140, 125; 216/56, 216/57
See application file for complete search history.

(56) References Cited
U.S. PATENT DOCUMENTS

| | | | |
|---|---|---|---|
| 6,261,469 B1 * | 7/2001 | Zakhidov et al. ........... 216/56 |
| 6,671,097 B2 * | 12/2003 | Fink et al. ................ 359/586 |
| 2001/0019037 A1 * | 9/2001 | Zakhidov et al. ............ 216/56 |
| 2006/0120683 A1 * | 6/2006 | Kamp et al. ................ 385/141 |
| 2006/0188398 A1 * | 8/2006 | Yano et al. .............. 422/82.01 |

* cited by examiner

*Primary Examiner*—Brian M. Healy
(74) *Attorney, Agent, or Firm*—Hill & Schumacher; Lynn Schumacher

(57) ABSTRACT

The present invention provides a straightforward and robust synthetic process for producing a chromatographic column with eluent-sensitive light diffracting properties based on an inherent photonic band structure and a chromatographic device using the chromatographic column. The present invention provides chromatographic devices employing a chromatographic column which in one embodiment is a photonic colloidal crystal which includes an assembly of colloidal microspheres assembled into a highly ordered array within a housing such as a tube with the highly ordered array being a photonic crystal along the length of the crystal, and a second embodiment which is an inverse construct of the first embodiment, where solid microspheres making up the photonic colloidal crystal chromatographic column are replaced with spherical voids or void spaces subsequent to infiltration of a material of selected refractive index. The photonic band structures of the first type of column made with colloidal particles and the second type of column made by inverting the first type of column may include a photonic band gap, a fundamental stop-band, higher stop-bands, or combinations thereof.

113 Claims, 13 Drawing Sheets

Figure 8
a)
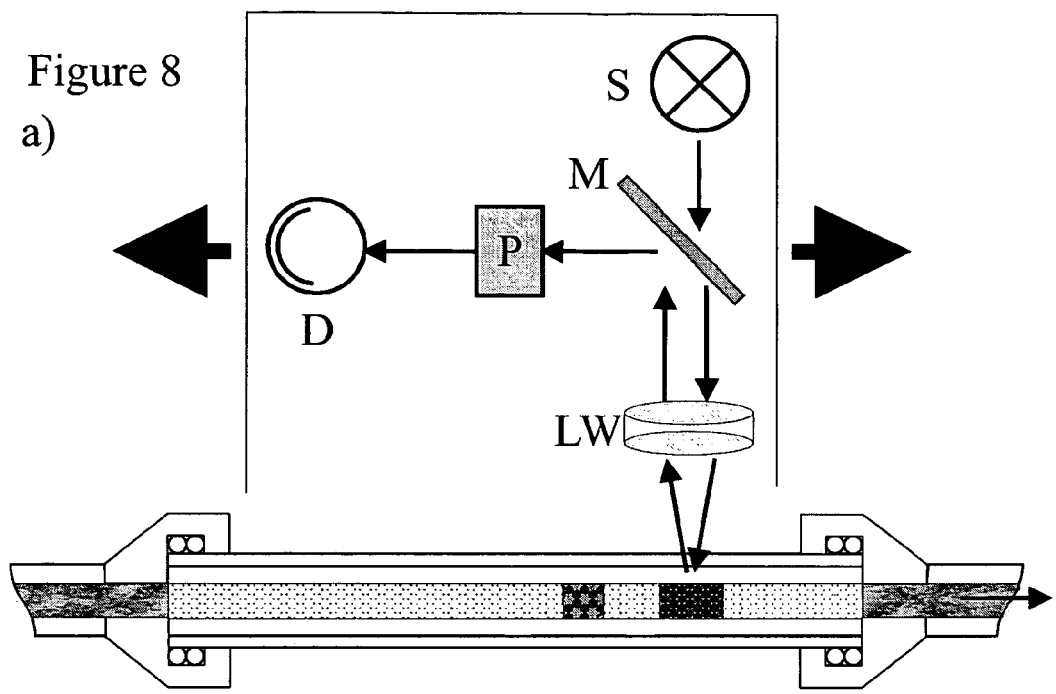
b)
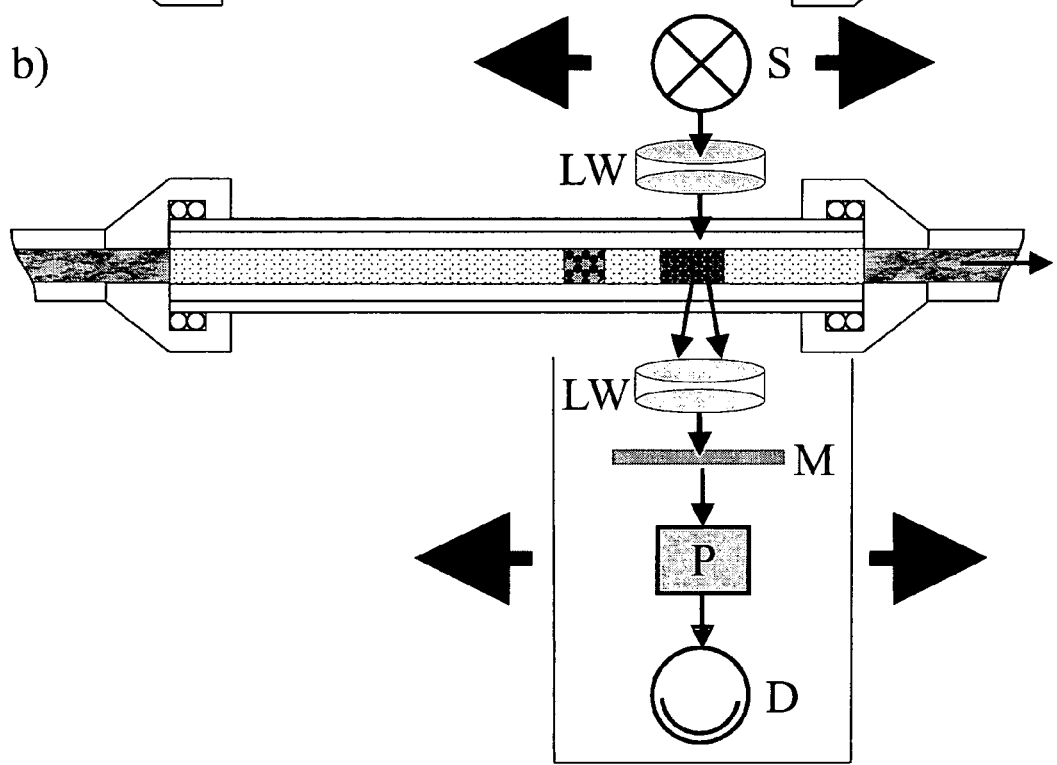

Figure 13
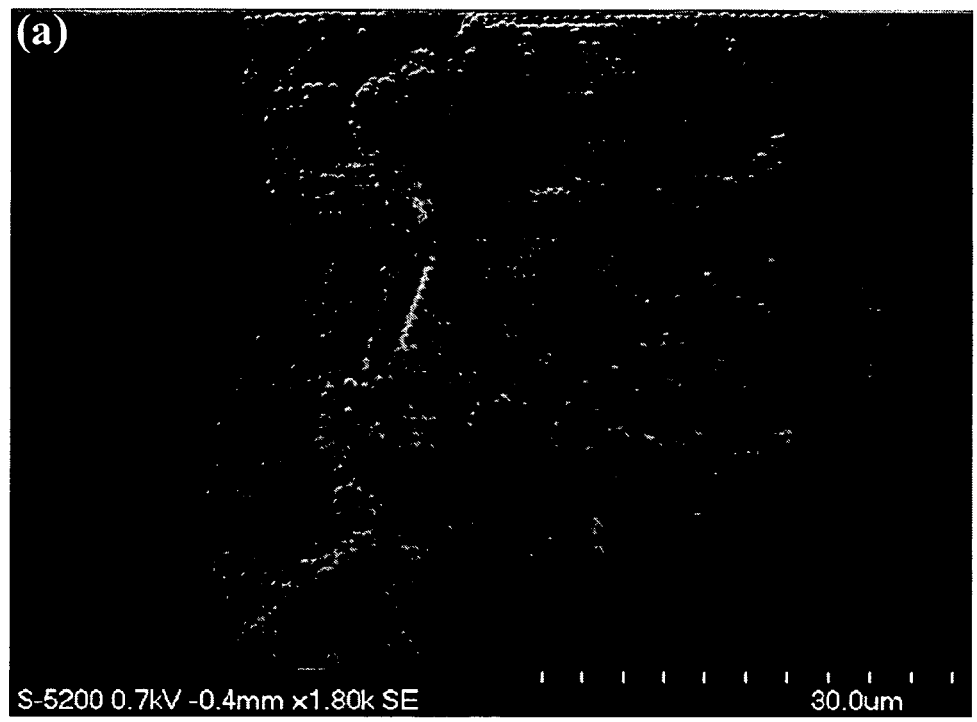
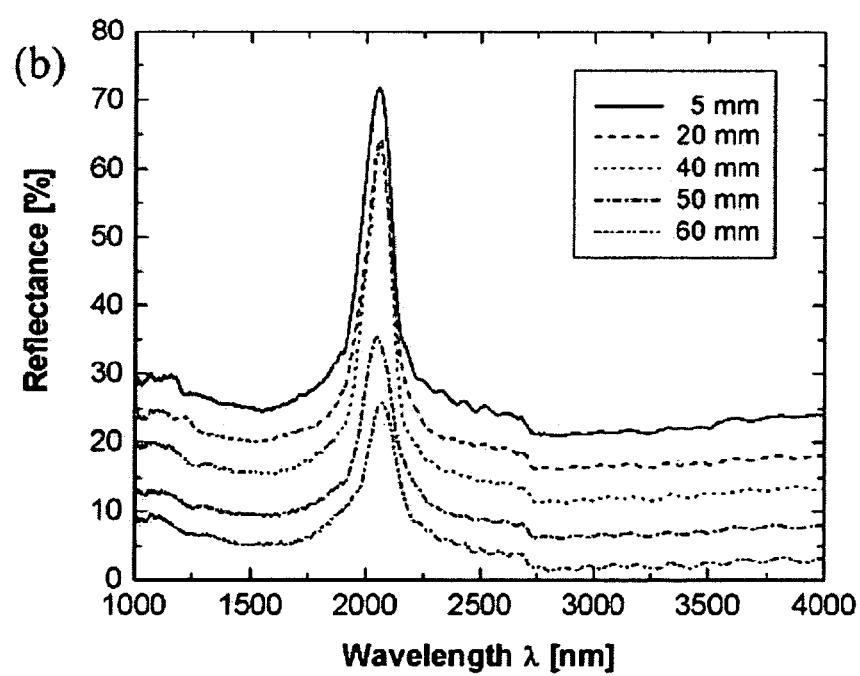

PHOTONIC COLLOIDAL CRYSTAL COLUMNS AND THEIR INVERSE STRUCTURES FOR CHROMATOGRAPHY

FIELD OF THE INVENTION

The present invention is directed to a chromatographic apparatus which includes a photonic colloidal crystal column produced using an assembly of colloidal microspheres, or a photonic crystal column produced by inversion of the column made of colloidal particles in which solid microspheres are replaced with interconnected spherical voids embedded in a material of pre-selected index of refraction. The photonic crystal columns are formed in a capillary and may be used in that form in the capillaries or removed from the capillaries and used as a free-standing column.

BACKGROUND OF THE INVENTION

Photonic Crystals

Photonic crystals interact strongly with electromagnetic radiation, when the periodicity of the photonic crystal corresponds to the scale of the wavelength of the electromagnetic radiation. The periodicity of the photonic crystal is achieved through a periodic modulation of the dielectric function. Due to the periodicity, photonic crystals display a photonic band structure with a fundamental stop-band as predominant feature for certain directions (see E. Yablonovitch, "Inhibited spontaneous emission in solid-state physics and electronics" Phys. Rev. Lett. 1987, 58, 2059; S. John, "Strong localization of photons in certain disordered dielectric superlattices" Phys. Rev. Lett. 1987, 58, 2486).

The promise for technological application in the optical properties of photonic crystals has sparked an enormous interest in methods of fabrication of photonic crystals. The main focus in future applications is directed towards the production of an all optical chip and integrated detector materials for optical sensing (see J. D. Joannopoulos, P. R. Villeneuve, S. Fan, "Photonic crystals: putting a new twist on light" Nature 1997, 386, 143; G. A. Ozin, S. M. Yang, "The race for the photonic chip: colloidal crystal assembly in silicon wafers" Adv. Funct. Mater. 2001, 11, 95; A. Arsenault, S. Fournier-Bidoz, B. Hatton, H. Miguez, N. Tetreault, E. Vekris, S. Wong, M. Y. San, V. Kitaev, G. A. Ozin, G. "Towards the synthetic all-optical computer: science fiction or reality?" J. Mater. Chem. 2004, 14, 781).

One common approach to photonic crystals is the self-assembly of spherical colloidal particles. Several methods have been developed to achieve colloidal crystal (often called "opal" due to the similarity with the gem structure) films of controlled thickness and various degrees of uniformity from spheres of varying diameters and materials (see P. Jiang, J. F. Bertone, K. S. Hwang, V. L. Colvin "Single-Crystal Colloidal Multilayers of Controlled Thickness" Chem. Mater. 1999, 11, 2132; S. Wong, S. Kitaev, S., G. A. Ozin "Colloidal Crystal Films: Advances in Universality and Perfection" J. Am. Chem. Soc. 2003, 125, 15589).

Infiltrating a photonic crystal with any other material in the form of a solid, gel, liquid, or gas causes a change in the photonic band structure and results in a shift of the fundamental stop-band (see R. C. Schroden, M. Al-Daous, C. F. Blanford, A. Stein, "Optical Properties of Inverse Opal Photonic Crystals" Chem. Mater. 2002, 14, 3305; C. F. Blanford, R. C. Schroden, M. Al-Daous, A. Stein, "Tuning solvent-dependent color changes of three-dimensionally ordered macroporous (3DOM) materials through compositional and geometric modifications" Adv. Mater. 2001, 13, 26; K. Yoshino, K. Tada, M. Ozaki, A. A. Zakhidov, R. H. Baughman, "The optical properties of porous opal crystals infiltrated with organic molecules" Japanese Journal of Applied Physics, Part 2: Letters 1997, 36(6A), L714).

For a non-swelling and inert colloidal photonic crystal material, its lattice parameters and structure will remain unchanged upon infiltration with a liquid. The values of refractive indices and refractive index changes can thus be measured via spectra taken from infiltrated colloidal crystals. The limiting factors are the structural or optical quality and uniformity of the photonic crystal and the resolution of the measuring instrument.

Colloidal Crystal Sensor Arrays

Colloidal particles can be assembled and embedded in a chemically responsive matrix, usually a gel incorporating ligands or binding sites selective to specific chemical moieties. Especially cross-linked colloidal crystal arrays have been extensively researched with regard to their potential applications as chemical sensors. The gels swell either in the presence of a liquid or swell selectively in the presence of a chemical moiety in that liquid or solvent. The lattice parameter changes due to the swelling and the optical behavior can be spectroscopically monitored (see J. H. Holtz; S. A. Asher, "Polymerized colloidal crystal hydrogel films as intelligent chemical sensing materials" Nature 1997, 389, 829; E. Reese, M. E. Baltusavich, J. P. Keim, S. A. Asher "Development of an intelligent polymerized crystalline colloidal array colorimetric reagent" Anal. Chem. 2001, 73, 5038).

Thus, the presence of a swelling liquid or a specific chemical entity can be detected by a shift in the band structure. It is problematic though to accurately determine refractive index variations as not only the index of the infiltrating liquid changes but also the refractive index of the colloidal crystal array changes, as the distance between spherical particles or void spaces is subject to change. This change is also non-linear as the swelling of the gel matrix is limited by the degree of cross-linking. The detection of rapid changes of solvent or mobile phase mixtures is also limited by diffusion and inertia or response time of the gel. These problems do not arise in the invention disclosed herein as the spheres of the photonic crystal column or wall materials used to produce the inverted crystal column do not react physically or chemically with the mobile phase.

Colloidal Crystal Arrays and Entropic Entrapping Chromatography

Arrays of air-spheres, void spaces or water-spheres embedded in a hydrogel displaying light diffraction have been manufactured and claimed for chromatographic separation applications (see Hydrogels with crystalline colloidal array of water voids for macromolecule separations and detection, Asher, Sanford A.; Liu, Lei. (University of Pittsburgh, USA). PCT Int. Appl. (2000), 48 pp. CODEN: PIXXD2 WO 2000000278 A1 20000106; Liu L., Li P., Asher S. A. Entropic trapping of macromolecules by mesoscopic periodic voids in a polymer hydrogel. Nature (1999 Jan. 14), 397(6715), 141-4).

The invention in the above patent by Asher et al. is restricted to macromolecules with linear chains that can assume one of a number of shapes from spherical to rod-like including a conformation with a maximum of conformational entropy. The rod-like or elongated shapes diffuse through the gel matrix into the isolated water-voids there to be entrapped after assuming an entropically favorable shape. Additionally, for the hydrogel to selectively entrap by an entropic effect, molecules of one certain average mass, equilibrium times of three to ten days are required.

After macromolecules of one certain average mass have been trapped, they have to partition back into a mobile phase, which will also take considerable time. The size of the template spheres has to be tailored for macromolecules of one specific average mass. One the other hand, the invention disclosed herein achieves separation by molecule-surface interaction of the materials to be separated contained in a mobile phase and the surface of the photonic colloidal crystal column or inverse photonic crystal column, not by entropic trapping. Thus there is no restriction regarding shape and size of molecules that can be separated.

While the molecules to be separated have to permeate through the hydrogel to the water voids, all mass transport in the present invention is achieved by a continuous mobile phase motion through the interstitial voids or connecting pores. Open mesopores enhance the separation but do not participate in the mass transfer. The present invention avoids the problems associated with hydrogel swelling, which would interfere with the monitoring of the spectral properties. The present invention is also advantageous in that the void and pore dimensions are invariant to solvent and temperature changes.

In the prior art, water void arrays of hydrogels have not been produced in capillaries, where the contact area between the confined hydrogel and a macromolecule solution is much smaller than with described hydrogel films and a macromolecule solution, and hence the partitioning would take much longer (see Hydrogels with crystalline colloidal array of water voids for macromolecule separations and detection. Asher, Sanford A.; Liu, Lei. (University of Pittsburgh, USA). PCT Int. Appl. (2000), 48 pp. CODEN: PIXXD2 WO 2000000278 A1 20000106; Liu L., Li P., Asher S. A. Entropic trapping of macromolecules by mesoscopic periodic voids in a polymer hydrogel. Nature (1999 Jan. 14), 397(6715), 141-4).

Monolithic Columns Made from Colloidal Crystals

The structural integrity is a prerequisite for future applications of photonic crystal materials and stationary phases. An isotropic monolithic material ensures uniform optical quality and consistent separation properties. This is achieved in the invention disclosed herein and has not been realized so far using other approaches.

Colloidal Crystals in Capillaries

Until recently, capillaries have been only completely filled with colloidal crystals by sedimentation, a process that requires weeks or months for completion if not assisted by gravity (centrifugation). The resulting capillary photonic crystals produced are not of the highest quality, especially using centrifugation, and their optical properties have not been investigated thoroughly with respect to axial and rotational uniformity. Due to the time requirements it is prohibitive to produce photonic crystal capillaries in the centimeter range by this method. (see W. L. Vos, R. Sprik, A. van Blaaderen, A. Imhof, A. Lagendijk, G. H. Wegdam "Strong effects of photonic band structures on the diffraction of colloidal crystals" Phys. Rev. B: Condens. Matter 1996, 53, 16231).

Colloidal crystal surface coatings have been produced in capillaries, which requires a meticulous control of the meniscus of the colloidal dispersion. A colloidal dispersion is pressed into a capillary, where the capillary rests in a temperature regulated environment. The meniscus and thus the microsphere deposition is controlled by adjusting the evaporation rates via temperature and by controlling the velocity of the dispersion liquid. These surface coating films presented in prior art are mostly monolayers of microspheres, or a continuous multi-layer coatings, but complete filling has not been achieved by this method. Additionally, high film quality or the order of the colloidal particles shown in the following reference is yet to be achieved. Spectral data of monolayers or multi-layers of colloidal crystals have not been reported (see H. Wang, X. Li, H. Nakamura, M. Miyazaki, H. Maeda, "Continuous Particle Self-Arrangement in a Long Microcapillary" Adv. Mater. 2002, 14, 1662).

Microsphere monolayer coatings in capillaries might become interesting for gas chromatographic application and catalytic purposes, but they cannot be applied in liquid chromatography applications, which require continuous packed phases. This problem has been overcome by the invention disclosed herein.

Colloidal crystallization and banding of microspheres in capillaries has been examined, but the morphology and spacing of the bands were not uniform. These structures are not suitable for spectroscopy of stop-bands or chromatography. The height of the microsphere dispersion column is solely determined by the contact angle and inner diameter of the employed capillary. Crystallization is induced by solvent evaporation at elevated temperatures (see M. Abkarian, J. Nunes, H. A. Stone, "Colloidal Crystallization and Banding in a Cylindrical Geometry", J. Am. Chem. Soc. 2004, 126, 5978).

The spacing of the bands is strongly dependent upon the growth conditions, which leads to irregular spacing and banded (striped) structures if not meticulously controlled. The micromolding in capillaries (MIMIC) technique has been used to confine the nucleation and growth of photonic colloidal crystals to microchannels fashioned in a polydimethylsiloxane (PDMS) elastomeric stamp held in conformal contact with a planar substrate. Thus the capillary is formed by combining the PDMS channel with a flat substrate. Alternatively a channel or a groove in a substrate could be covered by a flat PDMS stamp to construct an enclosed capillary. The PDMS mold does not allow the operation of a pressure driven mobile phase. For chromatographic applications it is necessary to utilize a method which produces well-ordered colloidal crystals inside pressure-resistant capillary tubes. MIMIC delivers capillary photonic crystal structures but optical properties have never been reported for these structures, but nevertheless these structures are not suitable for separation applications (see E. Kim, Y. Xia, G. M. Whitesides, "Micromolding in Capillaries: Applications in Materials Science", J. Am. Chem. Soc. 1996, 118, 5722).

Similar limitations apply to other related methods of the formation of ordered colloidal crystals with excellent optical properties in channels or grooves etched in templates (see S. M. Yang, H. Miguez, G. A. Ozin, G. A., "Opal circuits of light—planarized microphotonic crystal chips" Adv. Funct. Mater. 2002, 12, 425).

Colloidal particle arrays in capillaries have also been manufactured by employing capillary forces and not pressure to partially fill capillaries with a colloidal dispersion. After the capillary has been partially filled the fiber is removed from the dispersion reservoir. The length of the colloidal crystal is solely determined by the combination of capillary diameter and the dispersion concentration (see J. H. Moon, S. Kim, G.-R. Yi, Y.-H. Lee, S.-M. Yang, "Fabrication of Ordered Macroporous Cylinders by Colloidal Templating in Microcapillaries" Langmuir 2004, 20, 2033).

The above-mentioned article is also restricted to cylindrical capillaries and the optic properties for template constructs and inverse constructs have not been examined.

These structures have not been infiltrated with liquids and there has not been any teaching in respect of chromatographic applications.

Monoliths History

Conventional liquid chromatography columns are uniform packings of roughly spherical porous particles. Separation of compound mixtures occurs via mass transfer of analytes into and out of diffusive particle pores. The diffusion rate of the separation is limited by the pores and their structural variance and poses a major source of band broadening in the resulting chromatogram. Smaller porous particles shorten the diffusive path length, improve mass transfer and provide better separation efficiency (see R. E. Majors, "Advances in the design of HPLC packings" *LC GC North America* 2000, 18, 586; R. E. Majors, "HPLC column packing design" *LC GC Europe* 2003, 16, 8; R. E. Majors, "A review of HPLC column packing technology" *Am. Lab.* 2003, 35, 46).

Driven by improvement in separation efficiency, column permeability is concomitantly decreased and thus the column back-pressure is greatly increased. These limitations are overcome by monolithic columns, employed as continuous separation beds or phases in liquid chromatography (LC) or in capillary electrochromatography (CEC). When discussing monolithic structures, the terms and concepts of particles and interstitial voids have to be replaced (see G. Rozing, "Trends in HPLC column formats—microbore, nanobore and smaller" *LC GC Europe* 2003, 16, 14).

A continuous porous structure has to be considered instead, consisting of through-pores or macropores and smaller mesopores. The macropores provide permeability and efficiency, while drastically reducing the pressure drop along the column. (see R. E. Majors, "Advances in the design of HPLC packings" *LC GC North America* 2000, 18, 586; R. E. Majors, "HPLC column packing design" *LC GC Europe* 2003, 16, 8; R. E. Majors, "A review of HPLC column packing technology" *Am. Lab.* 2003, 35, 46; G. Iberer, R. Hahn, A. Jungbauer, "Column watch: Monoliths as stationary phase for separating biopolymers—fourth-generation chromatography sorbents" *LC GC North America* 1999, 17, 998; R. E. Majors, *LC GC North America* 2001, 19, 1186; F. Svec, *LC GC Europe* 2003, 16, 24).

Monoliths are cast as homogeneous phases in situ and can potentially be used directly as columns. The porous structure is templated by dispersing a non-miscible monomeric component (porogen) and a polymerizable inorganic component in a mold or capillary and simultaneously initializing polymerization of both components. The polymerized phases can be removed separately resulting in a porous structure (see S. Hjertén, J.-L. Liao., R. Zhang "High-performance liquid chromatography on continuous polymer beds" *J. Chromatogr. A* 1989, 473, 1, 273; F. Svec, J. M. J. Fréchet, "Continuous rods of macroporous polymer as high-performance liquid chromatography separation media" *Anal. Chem.* 1992, 64, 820; H. Minakuchi, K. Nakanishi, N. Soga, N. Ishizuka, N. Tanaka, "Octadecylsilylated Porous Silica Rods as Separation Media for Reversed-Phase Liquid Chromatography" *Anal. Chem.* 1996, 68, 19, 3498). Control over pore sizes can be exerted to a certain degree and a double-pore structure has been disclosed (see N. Ishizuka, H. Minakuchi, K. Nakanishi, N. Soga, N. Tanaka, *J. Chromatogr. A* 1998, 797, 133). However, the size distribution of mesopores and macropores in these stationary phases is usually broad and the pore morphology is random (see H. Minakuchi, K. Nakanishi, N. Soga, N. Ishizuka, N. Tanaka, *Anal. Chem.* 1996, 68, 19, 3498; N. Ishizuka, H. Minakuchi, K. Nakanishi, N. Soga, N. Tanaka, *J. Chromatogr. A* 1998, 797, 133; N. Ishizuka, H. Minakuchi, K. Nakanishi, K. Hirao, N. Tanaka, *Coll. And Surf. A* 2001, 187-188, 273). So far, no monolithic separation phases have been presented or produced that have a bimodal pore structure with a size distribution as narrow and with a pore structure as ordered as the photonic crystal columns disclosed herein made of colloidal particles or photonic crystal columns produced by inverting the columns made of the colloidal particles. The use of polymeric porogens to produce monolithic separation beds in capillaries does not produce structure having sufficient 3-D periodical ordering to generate a change in photonic band gap structure upon interaction with electromagnetic radiation.

An incentive for the development of monolithic columns is the absence of a frit needed in conventional particulate columns to contain the separation medium particulates. The frit is a source of analyte spreading, which decreases separation efficiency. Its omission presents a major advantage in column technology.

The filling of capillaries with beads or microspheres usually requires the presence of a frit to contain the microparticles inside the capillary. Such frits contribute to the peak broadening in the chromatogram, due to inferior structural order, the additional diffusive path length, and/or different interaction of the analytes as stationary phase and frit are made from different materials. For bead templated porous monolithic columns the initial frits are produced by tapping one end of the capillary into a paste prepared from the utilized silica particles and a silicate solution. The resulting plug is fused in situ (see G. S. Chirica, V. T. Remcho, "Novel monolithic columns with templated porosity" *Journal of Chromatography A* 2001, 924, 223).

Monolithic Columns Based on Colloidal Crystal Templates

Monolithic columns with bead templated porosity have been produced in capillaries. Silica beads were packed into capillaries prior to flushing the bead array with a monomer solution. After polymerization of the monomeric components the silica beads were removed by aqueous wet etching (see G. S. Chirica, V. T. Remcho, "Novel monolithic columns with templated porosity" *Journal of Chromatography A* 2001, 924, 223). Despite using a template structure no photonic band structure is generated, the material is irregular and lacks the necessary periodicity of the invention disclosed herein.

SUMMARY OF THE INVENTION

An objective of the present invention is to provide a straightforward and robust synthetic process for producing a chromatographic column with eluent-sensitive light diffracting properties based on an inherent photonic band structure and a chromatographic device using the chromatographic column.

The present invention provides chromatographic devices employing a chromatographic column which, in one embodiment, is a photonic colloidal crystal which includes an assembly of colloidal microspheres formed into a column, and which, in a second embodiment is the inverted structure of the first embodiment, where solid microspheres making up the photonic colloidal crystal chromatographic column are replaced with spherical voids or void spaces subsequent to infiltration of a material of selected refractive index. Thus, the present invention provides two different types of photonic crystal columns. The first type is prepared using colloidal crystal particles assembled into a highly ordered array of particles within a housing such as a tube with the highly ordered array being a photonic crystal along the length of the crystal. The second type of photonic crystal column is produced by inverting the first type of photonic crystal column by infiltrating in a material of selected refractive index and removing the original colloidal particles to leave behind air voids. The material is selected to ensure it provides sufficient refractive index with the air voids so that the crystal column is a photonic crystal column.

Thus, in one aspect of the invention there is provided a chromatographic separation medium, comprising:

an elongated housing containing a photonic crystal column enclosed therein having a photonic band structure which interacts selectively with electromagnetic radiation along a length of the photonic crystal column, the photonic crystal column including interconnected voids defining flow passageways through the photonic crystal column for a liquid, gaseous, critical, or supercritical mobile phase containing materials to be separated by the photonic crystal column, wherein changes in the photonic band structure of the photonic crystal column occur as the liquid, gaseous, critical, or supercritical mobile phase containing materials to be separated is flowed through said photonic crystal column and separated therein.

In another aspect of the invention there is provided a method of producing a photonic crystal column having a photonic band structure which interacts with electromagnetic radiation along a length of the photonic crystal column, the photonic crystal column including interconnected voids defining flow passageways through the photonic crystal column for a liquid, gaseous, critical, or supercritical mobile phase containing materials to be separated by the photonic crystal column, the method including the steps of:

a) preparing a dispersion of colloidal particles in a dispersion medium and flowing the dispersion through a first open end of an elongated housing until a colloidal dispersion droplet forms at a second open end of the elongated housing wherein evaporation of the dispersion medium leads to formation of a colloidal crystal plug at the second open end, which continuously grows into the elongated housing due to evaporation at the second open end or evaporation through pores of the elongated housing, causing dispersion medium depletion between the colloidal particles and directing colloidal crystal formation; and b) exerting pressure on the colloidal dispersion column along the first open end of the elongated housing for generating a force drawing the colloidal dispersion into the capillary after formation of the colloidal crystal plug wherein a colloidal crystal column grows inside the elongated housing and the dispersion medium evaporates out of the elongated housing, the colloidal particles being selected to give a colloidal photonic crystal column with interconnected voids between the colloidal particles defining flow passageways through the colloidal photonic crystal column and substantially uniform optical properties along the length of the column having a photonic band structure which interacts with electromagnetic radiation.

In this aspect of the method, the photonic crystal column produced using colloidal particles may be inverted to produce a second type of photonic crystal column, prepared by the steps of:

infiltrating a gas, melt, liquid, or solution being a precursor or containing a precursor of a selected material into the flow passageways through the colloidal photonic crystal column formed by the interconnected void spaces between the colloidal particles;

inducing growth of the selected material in the void spaces from the precursor; and removing the colloidal particles to leave behind an inverted photonic crystal column comprised of the selected material forming the second photonic crystal column having interconnected voids formed by removing the colloidal particles defining flow passageways through the second colloidal photonic crystal column and having substantially uniform optical properties along the length of the column having a second photonic band structure which interacts with electromagnetic radiation along a length of the photonic crystal.

In another aspect of the invention there is provided a chromatographic method, comprising the steps of:

flowing a liquid, gaseous, critical, or supercritical mobile phase containing materials to be separated through a chromatographic separation medium which includes a photonic crystal column, the photonic crystal column having a photonic band structure which interacts with electromagnetic radiation along a length of the photonic crystal column, the photonic crystal column including interconnected voids defining flow passageways therethrough, wherein changes in the photonic band structure of the photonic crystal column occur as the liquid, gaseous, critical, or supercritical mobile phase containing materials to be separated is flowed through said photonic crystal column and separated therein; and spectroscopically monitoring for changes in the photonic band structure of the photonic crystal column as the liquid, gaseous, critical, or supercritical mobile phase flows through the photonic crystal column and correlating any changes in the photonic band structure with the materials being separated.

The photonic band structures of the first type of column made with colloidal particles and the second type of column made by inverting the first type of column may include one of a photonic band gap, a fundamental stop-band, higher stop-bands, and combinations thereof.

BRIEF DESCRIPTION OF THE DRAWINGS

The general process of producing colloidal photonic crystal columns or inverse colloidal crystal columns according to the present invention will now be described, by way of example only, reference being made to the accompanying Figures, in which:

FIG. 1a) shows a cross section of a capillary assembly being filled with a colloidal dispersion column;

FIG. 2a) shows a cross section of a device for pressurizing the filled capillary tube which includes a colloidal dispersion reservoir and a capillary rigidly connected to this reservoir by a seal with a piston assembly for pressurizing the capillary;

FIG. 3a) shows a colloidal crystal capillary column made of colloidal particles prior to inversion to produce the inverted colloidal crystal column;

FIG. 4a) shows a first photonic crystal column or second photonic crystal column based device hermetically connected by seals or suitable connectors to a closed system that regulates the flow of a mobile phase or eluent;

FIG. 5a) shows a cross section of an elongated housing with a cylindrical tubing coated with a jacket material;

FIG. 8a) shows a photonic crystal column coupled with another optical system for monitoring the photonic band structure of the photonic crystal column as material is separated in the columns;

FIG. 8b) shows a photonic crystal column coupled with another optical system for monitoring the photonic band structure of the photonic crystal columns as material is separated in the columns;

FIG. 10a) shows the dependence of the wavelength ($\lambda$) of the stop band maximum on axial translation, for all data sets shown, solid and dashed lines represent mean averages and standard deviations, respectively;

FIG. 12a) shows the shift of the fundamental stop band, starting with a dry photonic crystal column and progressing by subsequently flowing octane, nonane, and decane through the photonic crystal column;

FIG. 13 displays the structure and optical properties of a photonic crystal column in a capillary with a square cross-section;

FIG. 13a) shows the cross-section of a square capillary, the photonic crystal column was produced inside the square capillary from 850 nanometer polystyrene microspheres by PACMAC, all faces of the photonic crystal column display the {111} plane of an fcc colloidal crystal.

FIG. 13b) shows that the photonic crystal column displays uniform optical behavior in the near infrared over centimeter-long distances. The photonic band structure is nearly invariant to translation along the capillary axis.

DETAILED DESCRIPTION OF THE INVENTION

Figure 1:
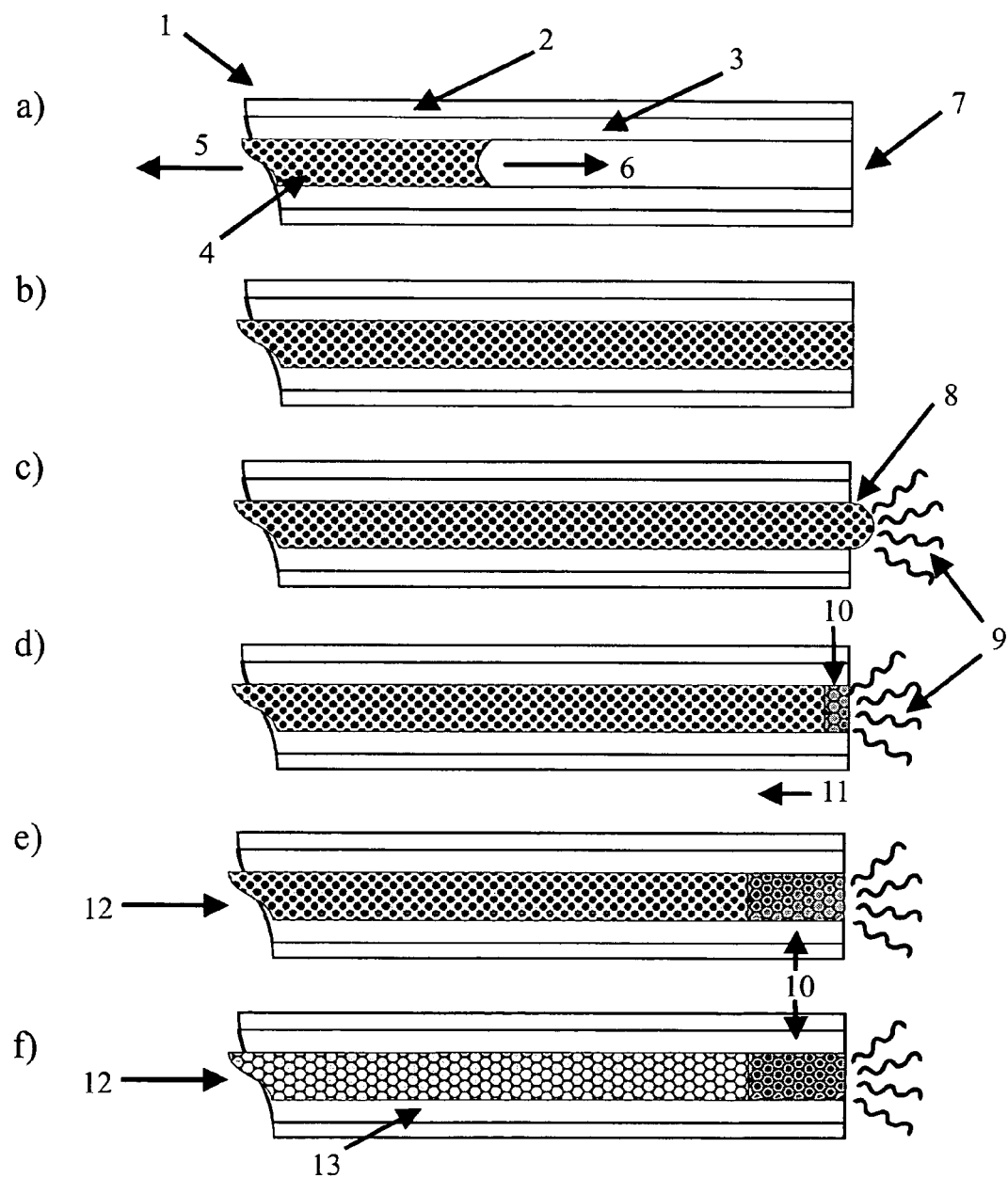
FIGS. 1a) to 1f) illustrate the different steps in a process of producing a colloidal crystal capillary column or first photonic crystal column inside a capillary or tube using pressure-assisted colloidal microsphere assembly in capillaries (PACMAC)
FIG. 1b) shows the capillary assembly completely filled with the colloidal dispersion.
FIG. 1c) shows a droplet of the colloidal dispersion formed at one of the open ends of the capillary assembly.
FIG. 1d) shows the colloidal dispersion in the capillary assembly with a colloidal crystal plug formed at one end of the capillary.
FIG. 1e) shows the stage of the colloidal plug growth, where the plug reaches a certain length and is capable of withstanding some mechanical force.
FIG. 1f) shows growth of a colloidal crystal capillary column made of colloidal particles induced by pressure being exerted on the colloidal dispersion column.

The present invention describes chromatographic devices employing a chromatographic column which, in one embodiment, is a photonic colloidal crystal which includes an assembly of colloidal microspheres formed into a column, and which, in a second embodiment is the inverted structure of the first embodiment, where solid microspheres making up the photonic colloidal crystal chromatographic column are replaced with spherical voids or void spaces embedded in a material of pre-selected index of refraction, in an elongate housing such as a capillary or as a free-standing column. Thus, the present invention provides two different types of photonic crystal columns, the first type of which is prepared using substantially monodisperse colloidal crystal particles assembled into a highly ordered array of particles within a housing such as a tube with the highly ordered array being a photonic crystal along the length of the crystal. The second type of photonic crystal column is produced by inverting the first type of photonic crystal column by infiltrating into it a material of selected refractive index and removing the original colloidal particles to leave behind air voids and the material is selected to ensure it provides sufficient refractive index with the air voids so that the crystal column is a photonic crystal column. Both types may be removed from their housings to give free standing structures.

Growing photonic crystals in capillaries is a method to synthesize high quality colloidal photonic crystals, which is clearly distinct from other methods to produce colloidal crystal films. Photonic crystal columns may be made having a length in the range from micrometers ($\mu$m) to meters (there being no inherent limitation of the length of the columns that can be produced) displaying high structural and optical quality and uniformity, while manufacturing requires only up to hours for producing columns of lengths of several millimeters and a couple of days for several centimeters. The degree of spectral uniformity obtained in the reference of Wong et. al. (S. Wong, S. Kitaev, S., G. A. Ozin "Colloidal Crystal Films: Advances in Universality and Perfection" *J. Am. Chem. Soc.* 2003, 125, 15589) is exceeded by the photonic crystal columns disclosed in the present invention. The photonic band structure includes photonic bandgaps, stop-band or stop-bands for both types of photonic crystals and the photonic crystal columns are invariant to rotation along the capillary axis in capillaries with circular cross section and translation over several centimeters along the capillary axis in capillaries of circular, elliptical, square, rectangular, triangular and hexagonal cross section.

The structural and optical quality and uniformity of the colloidal crystal columns is independent of the colloid particle size or choice of microsphere material (e.g. silica, polystyrene, polymethylmethacrylate), thus yielding invariant photonic band structure properties in the ultraviolet, visible, or infrared range of the electromagnetic radiation, the spectral range is determined by the employed colloidal particle size (see U. Kamp, G. von Freymann, V. Kitaev, S. A. Mabury, G. A. Ozin "Colloidal Crystal Capillary Columns—Towards Optical Chromatography" *Adv. Mater.*, manuscript accepted for publication, manuscript number: adma.200400020).

The process described herein to produce the colloidal crystal capillary columns has been termed pressure-assisted colloidal-microsphere assembly in capillaries (PACMAC). The developed and disclosed process of PACMAC is also extremely robust, independent of capillary orientation, insensitive to changes in environmental conditions and vibrations. Furthermore, it is highly reproducible. The structure and position of the fundamental stop-band or stop-bands of photonic crystals and inverse photonic crystals depend on the crystal lattice dimensions, i.e. the microsphere or air-sphere diameter, the effective refractive index $n_{eff}$ and the filling fraction $\phi$ of the crystal-forming material (see V. N. Bogomolov, S. V. Gaponenko, I. N. Germanenko, A. M. Kapitonov, E. P. Petrov, N. V. Gaponenko, A. V. Prokofiev, A. N. Ponyavina, N. I. Silvanovich, S. M. Samoilovich, "Photonic band gap phenomenon and optical properties of artificial opals" *Phys. Rev. E* 1997, 55, 7619; C. Lopez, "Materials aspects of photonic crystals" *Adv. Mater.* 2003, 15, 1679).

In PACMAC, microspheres are self-assembled in capillaries to form monolithic colloidal photonic crystals. The capillaries are connected to a reservoir containing a colloidal dispersion. A colloidal crystal plug is formed first at one open end of the capillary by forcing a colloidal dispersion through the capillary from the other end until all the capillary is uniformly filled and a dispersion droplet is formed at the capillary open end. Evaporation of the dispersion solvent from the droplet at the open end induces solid colloidal plug formation, which progresses into the capillary. As soon as the colloidal plug is solidified and capable of withstanding some mechanical force, pressure is exerted on the reservoir containing the colloidal dispersion. The pressure can be generated by a piston, by gas pressure, or hydrostatic pressure acting directly or indirectly on the dispersion reservoir.

Alternatively, a capillary connected to a reservoir can be placed in a centrifuge or a reduced pressure environment, where the pressure is exerted by a centrifugal force or the pressure differential between the reservoir and the low-pressure environment. In the latter case, evaporation of the dispersion solvent is also facilitated. This process provides a chromatographic separation medium, which is a photonic crystal column enclosed in an elongated housing with the photonic crystal column having a photonic band structure which gives rise to optical diffraction along a length of the photonic crystal. The photonic crystal column includes interconnected voids between the colloidal crystal defining flow passageways through the photonic crystal column for a liquid, gaseous, critical, or supercritical mobile phase containing materials to be separated during flow through the photonic crystal column. Thus a solid and monolithic photonic colloidal crystal is formed inside the capillary, which is intended to be used as a chromatographic separation phase in one application.

Figure 2:
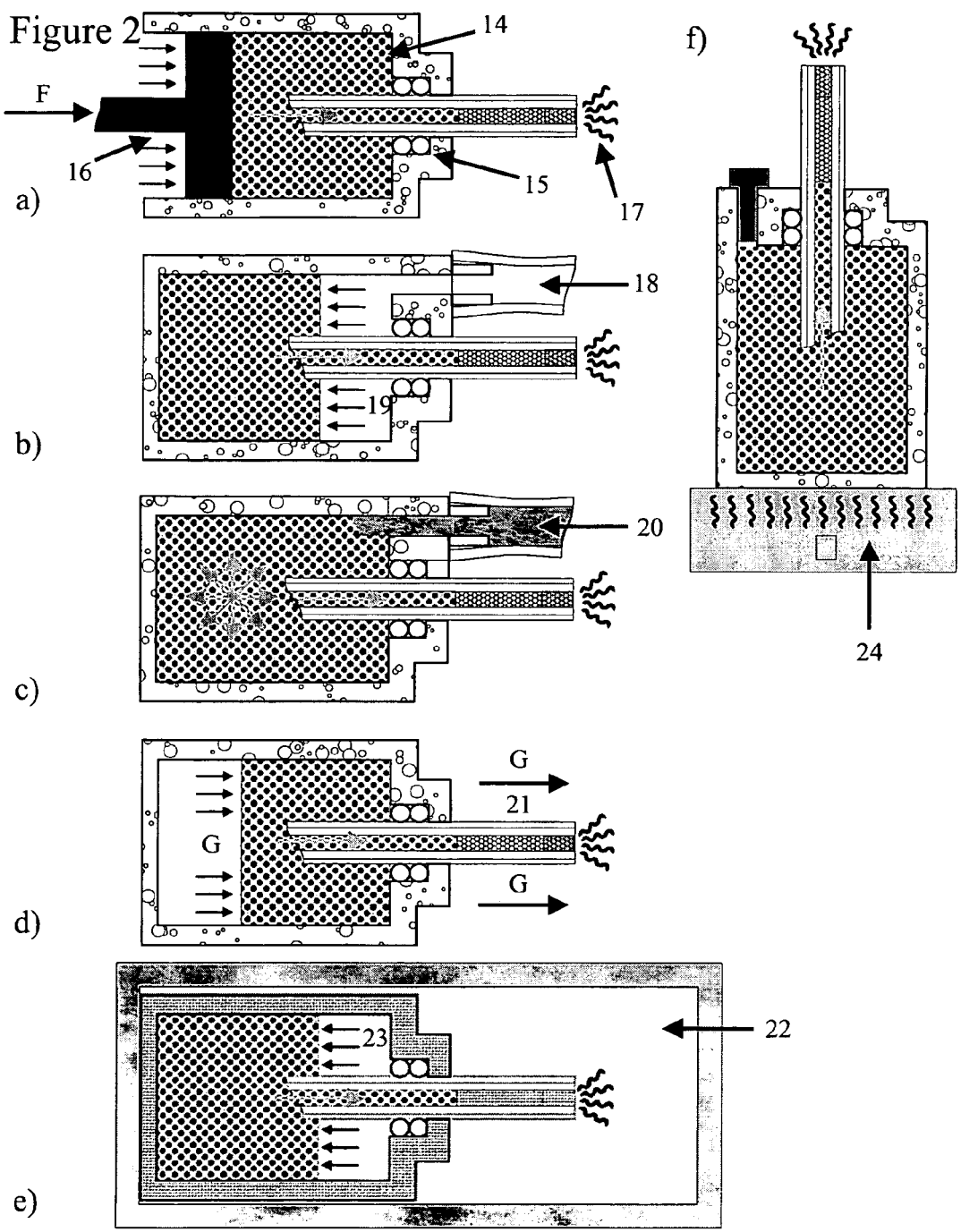
FIGS. 2a) to 2f) show various embodiments of devices, which may be used to generate pressure inside capillaries during the colloidal crystal growth after the colloidal plug has been formed.
FIG. 2b) shows an alternative embodiment device which may be used to generate pressure inside capillaries which is similar to the device of FIG. 2a) but instead of a piston it uses gas directed into the reservoir wherein the gas pressure exerts a force on the colloidal dispersion which generates a pressure in the dispersion column inside the capillary.
FIG. 2c) shows an alternative embodiment device which may be used to generate pressure inside capillaries which is similar to the device of FIG. 2b) but instead of using gas, pressure is exerted hydrostatically by pumping a liquid into the dispersion reservoir.
FIG. 2d) shows an alternative embodiment device which may be used to generate pressure inside capillaries in which the reservoir and capillary have been placed inside a centrifuge whereupon the centripetal force acts on the dispersion and the dispersion column inside the capillary.
FIG. 2e) shows an alternative embodiment device which may be used to generate pressure inside capillaries in which the reservoir-capillary assembly is placed in a reduced pressure system whereupon the pressure differential between the internal reservoir pressure and the external dynamic low pressure generates a force pushing the colloidal dispersion into the capillary.
FIG. 2f) shows an alternative embodiment device which may be used to generate pressure inside capillaries wherein the reservoir is heated so that the thermal expansion of the liquid forces the dispersion into the capillary.

The above discussed methods of producing photonic crystal columns and their inverse photonic crystal columns will now be discussed with particular reference to FIGS. 1, 2 and 3.

FIGS. 1a) to 1f) illustrate the process of producing a photonic crystal column made of colloidal crystal particles inside a capillary or tube. In FIG. 1a) an elongated housing or capillary assembly (1) with a jacket material (2), which can consist of multiple layers and can include polymers or metals, surrounding the capillary wall material (3), which can include a polymer, glass, fused silica, metal, etc., is shown. A colloidal dispersion column (4), comprised of colloidal particles with 50 nanometer to 3 micrometer diameter in a liquid dispersion medium (examples being water or ethanol or solvent mixtures), stemming from a dispersion reservoir (5) connected to the elongated housing (7) is forced through the elongated housing cavity in direction (6) towards the open end (7) of the elongated housing (7). The colloidal dispersion fills the capillary completely in FIG. 1b). The flow of the dispersion is maintained until a colloidal dispersion droplet (8) forms at the open end shown in FIG. 1c). Evaporation of the dispersion solvent (9) leads to the formation of a colloidal crystal plug (10), which continuously grows into the capillary (11) due to evaporation, causing solvent depletion between colloidal particles and directing colloidal crystal formation, as seen in FIG. 1d). FIG. 1e) shows the stage of the colloidal plug growth, where the plug reaches a certain length and is capable of withstanding some mechanical force. Pressure is exerted on the colloidal dispersion column (12). Under these conditions a photonic crystal column (13) is grown inside the elongated housing as shown in FIG. 1f). The shades of gray represent the differences in optical properties between the colloidal plug and the photonic crystal column, the lighter shade standing for high reflectivity and high optical quality. The length ratios between the photonic crystal column and the plug are not drawn to scale.

FIGS. 2a) to 2f) illustrate various methods to generate pressure inside the elongated housing during the colloidal crystal growth after the colloidal plug has been formed. FIG. 2a) shows a colloidal dispersion reservoir (14) and a capillary rigidly connected to this reservoir by a seal (15). A force F is exerted on a piston (16) pressing directly or indirectly on the colloidal dispersion in the reservoir. Dispersion solvent is forced to the open end of the capillary, where it evaporates (17). If the capillary is rigid and its wall is mechanically strong the capillary can act as a piston itself. As shown in FIG. 2b) gas can be fed into the reservoir (18), where the gas can be nitrogen, air or any other conceivable non-reactive gas. The gas pressure exerts a force on the colloidal dispersion (19), which generates a pressure in the dispersion column inside the capillary. Alternatively pressure can be exerted hydrostatically by pumping a liquid (20) into the dispersion reservoir (FIG. 2c). The liquid can be the colloidal dispersion itself, the dispersion liquid, or any non-miscible liquid, an inorganic oil, exemplified by silicone oil, or a fluorinated solvent exemplified by perfluorodecalin.

In FIG. 2d) the reservoir and the capillary have been placed inside a centrifuge, the centripetal force G acts on the dispersion and the dispersion column inside the capillary. A reduced pressure system (22) contains the reservoir-capillary assembly in FIG. 2e). The pressure differential between the internal reservoir pressure (23) and the external dynamic low pressure in the reduced pressure system (22) generates a force pushing the colloidal dispersion into the capillary. An advantage is the continuous removal of evaporated dispersion solvent in the reduced pressure apparatus as shown in FIG. 2f). The reservoir can also be heated by a suitable heating element (24) the thermal expansion of the liquid forces the dispersion into the capillary.

Once the colloidal crystal column has been produced in the elongated housing or capillary, the next steps are consolidation of the colloidal crystal within the substrate. For example, when silica colloidal crystals are used, consolidation of the silica colloidal crystal within the elongated housing may be achieved by a number of methods, including thermal sintering, or hydrothermal treatment in an aqueous medium in the presence of a silica precursor to give necking of the silica microspheres, or chemical vapour deposition (CVD) of a volatile silica precursor to connect the silica microspheres with a thin uniform coating of silica (see Miguez, Hernan; Ozin, Geoffrey Alan; Yang, San Ming; Tetreault, Nicolas. Mechanical stability enhancement by pore size and connectivity control in colloidal crystals by layer-by-layer growth of oxide. U.S. Pat. Appl. Publ. (2004), 16 pp. CODEN: USXXCO US 2004062700 A1 20040401 CAN 140:293287 AN 2004:267147). In the case of the sintering process, this leads to the necking, or the formation of small necks, between neighbouring silica spheres. Necking is the thermally induced softening and flow of silica into the regions defined by the touching of silica spheres in the colloidal silica crystal to create a silica neck with a diameter that facilitates infiltration of a material of pre-selected composition and refractive index into the voids of the silica opal and etching of silica from the infiltrated opal to create the inverse photonic crystal structures. Further details regarding the necking process steps are disclosed in co-pending U.S. patent application Ser. No. 010/255,578 filed Sep. 27, 2002, which is incorporated herein by reference in its entirety.

When polymer colloidal crystals are used, consolidation of the polymer colloidal crystal within the elongated housing may be achieved by a number of methods, including thermal treatment at elevated temperatures ranging from 60 to approximately 200° C. to facilitate necking between the individual microspheres. Therefore, by choosing a suitable temperature and time interval for the thermal treatment, the necking size can be controlled, and in a second photonic crystal column derived from this first photonic crystal column, the dimensions of the pores connecting the void spaces can be controlled. Chemical vapour deposition (CVD) methods can also be applied for consolidation, yielding a composite photonic crystal column made from polymer spheres and covered with another material enhancing the necking and thus mechanical stability of the column.

The PACMAC method of synthesis disclosed herein yields continuous colloidal photonic crystal columns with uniform optical properties along the length of the column, which can be 15 centimeter or more in length, which form the basis of a chromatographic separation medium. The length of the resulting photonic crystal column in the housing can be directly and visually determined by the opalescence of the colloidal photonic crystal. The photonic crystals produced by the method disclosed herein exhibit a photonic band structure, which may include either a photonic band gap, or a stop-band, or any combination thereof.

The changes in the photonic band structure of the photonic crystal column which occurs as a liquid, gaseous, critical, or supercritical mobile phase containing materials to be separated is flowed through the photonic crystal column and separated therein include changes in the photonic band structure upon changes in the refractive index of the mobile phase traveling through the photonic crystal column, which cause a shift in a wavelength of optical diffraction along the length of the photonic crystal that can be monitored spectroscopically.

The changes in the refractive index of the mobile phase may arise due to a change of the composition of the mobile phase constituents or due to the presence of dissolved chemical moieties. Spectrally prominent features of the photonic crystal column can be detected either in reflection or transmission or in combinations thereof in the ultraviolet, visible, near infrared, and/or infrared spectrum of electromagnetic radiation.

The housing can be composed of any material, such as but not limited to polymers, oxides, chalcogenides, glasses, metals and semiconductors, combinations and composites of aforesaid materials. For example, the housing can be composed of polymers such as polyetheretherketone (PEEK), oxides (glass, fused silica), chalcogenides (arsenic trisulfide), metals (steel, titanium, copper), semiconductors (silicon), etc., or combinations of different materials, with or without a jacket material covering the elongated housing or capillary, with an internal capillary surface suitable for, or specifically prepared by any kind of treatment, exemplified by acid pre-treatment (mixtures of hydrogen peroxide and concentrated sulfuric acid), hydrophobization (perfluorooctadecyl triclorosilane, octadecyl trichlorosilane), etc., for the self-assembly of microspheres.

The elongated housing can be rigid or flexible, and may have solid housing walls or the walls may be porous, with pore sizes less than the utilized microsphere diameter. First, pores will enhance evaporation of the liquid from the capillary through its pores upon preparation of a first photonic crystal column. Second, pores will enhance the preparation of the inverse structure or second photonic crystal column via facilitated material removal through the housing pores. Inner diameters of capillaries can range from about 10 micrometers to several centimeters, where the cavity cross-section can be square, rectangular, circular, elliptical, triangular, hexagonal or of any other arbitrary shape. The housing may be made of a material which is a transparent or partially transparent material in the ultra-violet, visible, near infrared and infrared spectral regions of the electromagnetic spectrum.

The elongated housing may include chemical surface patterns on the interior surface of the elongated housing wall in order to guide the microsphere deposition on the surface of the housing and produce the photonic colloidal crystal columns having a desired surface arrangement and photonic band structure. The elongated housing may include relief surface patterns on the interior surface of the elongated housing wall in order to guide the microsphere deposition on the surface of the housing and produce colloidal photonic crystal columns having a desired surface arrangement and photonic band structure.

The microspheres used in PACMAC can be of various diameters ranging from 50 nanometer to 3 micrometer and can be composed of various materials, including but not limited to inorganic materials, for example silica, titania, zirconia, alumina, magnesia, oxides, other ceramics, chalcogenides, borides, carbides, pnictides (compounds of phosphorus, arsenic, antimony, and bismuth, for room-temperature paramagnetic materials, etc.), silicides, metals, polymer materials, nano-crystals (including quantum dots and quantum rods), composites of aforesaid materials and spherical core-shell particles of combinations of aforesaid materials and hybrid materials (e.g. $SiO_xR_{y-x}$, where R is an organic functional group or bridging link), and particles having core-shell architecture (a quantum dot core with a polystyrene shell, a soft polymer core with a titania shell, etc.).

The polymer materials may for example be non-cross-linked or cross-linked polystyrene, polymethacrylates, polyacrylates, polyurethanes, polyketones, polybutadiene, inorganic polymers, metallopolymers, (e.g. polyferrocenosilane), copolymers, grafted polymers, block-copolymers, dendrimers, biopolymers and composites of aforesaid polymer materials.

The microspheres can be solid or porous, where the pores can be ordered or random, monodisperse or polydisperse. The polydispersity of the colloidal microspheres is in the appropriate range to allow the self-assembly of said spheres into ordered three-dimensional arrays that show optical properties of interest (e.g. a stop-band) in the spectral region of interest due to their photonic band structure.

The monodispersity of the colloidal particles used for formation of the photonic crystal columns made of colloidal particles and photonic crystal columns formed by inversion of these columns, allows for a nearly ideal and extremely dense packing of the chromatographic phase described in this invention.

The surfaces of the colloidal particles may be modified by, for example, plasma treatment in the presence of reactive (oxygen, fluoroalkanes, sulfur hexafluoride) or non-reactive gases, chemical agents which may involve physically or chemically immobilizing the agents on the surfaces of the particles, using etching agents (hydrofluoric acid), hydrophobic agents (perfluorooctadecyltrichlorosilane, octadecyltrichlorosilane for reversed phase surfaces), charge-altering and carrying agents (carboxy, amine, sulfate, sulfone-functionalized alkyltrichlorsilanes), functional group carrying agents (alkyltrichlorosilanes functionalized with fluorescent groups), surface-active molecules (chelating agents), biomolecular agents (immobilized anti-bodies, enzymes), nano-clusters (quantum dots, quantum rods) and polyelectrolytes (multilayers by electrostatic self-assembly).

The photonic crystal columns, contained within the elongated housings or as a separate free-standing columns after removal from the housings, exhibit a photonic band structures, which can can be monitored in reflection and transmission in selected or combined ranges of the ultraviolet, visible or infrared part of the electromagnetic spectrum.

The first type of a photonic crystal column can be inverted using suitable materials (including titania, zirconia, polymers) and consecutive removal of the original template structure (polystyrene, polymethylmethacrylate, silica). The resulting structure also exhibits a photonic band structure. For the formation of the second type of photonic crystal column by inversion, any precursors are suitable that can be melted, liquefied, dissolved, suspended, dispersed, or evaporated, that can pass through the interstitial voids of the first type of photonic crystal column made of colloidal particles in their respective states, that can deposit in the interstitial space and that do not destroy the original template.

The inversion materials and their precursors can be monomeric, polymeric, organic, inorganic, metallic, nano-particulate (silica or titania nano-particles or quantum dots), or a mixture or a composite of the aforementioned materials. Liquids (bulk titanium tetrabutoxide, sol-gel precursors in solution), melts (example suitable ferrocenophanes), and mixtures (titanium tetrabutoxide, tetramethyl orthosilicate) infiltrate the photonic crystal column by capillary force action upon contact with the inversion material, they can be pressed through the photonic crystal column, or they can be forced into the interstitial voids by applying a vacuum at the open end of the capillary. Gaseous precursors (including tetramethyl orthosilicate, tetrachlorosilane, disilane, etc.) can be streamed through the photonic crystal column, while the capillary is kept in conditions suitable for a respective chemical vapor deposition. Further details regarding the inversion step may are found in co-pending U.S. patent application Ser. No. 09/977,254 filed Oct. 16, 2001, which is incorporated herein by reference in its entirety.

Figure 3:
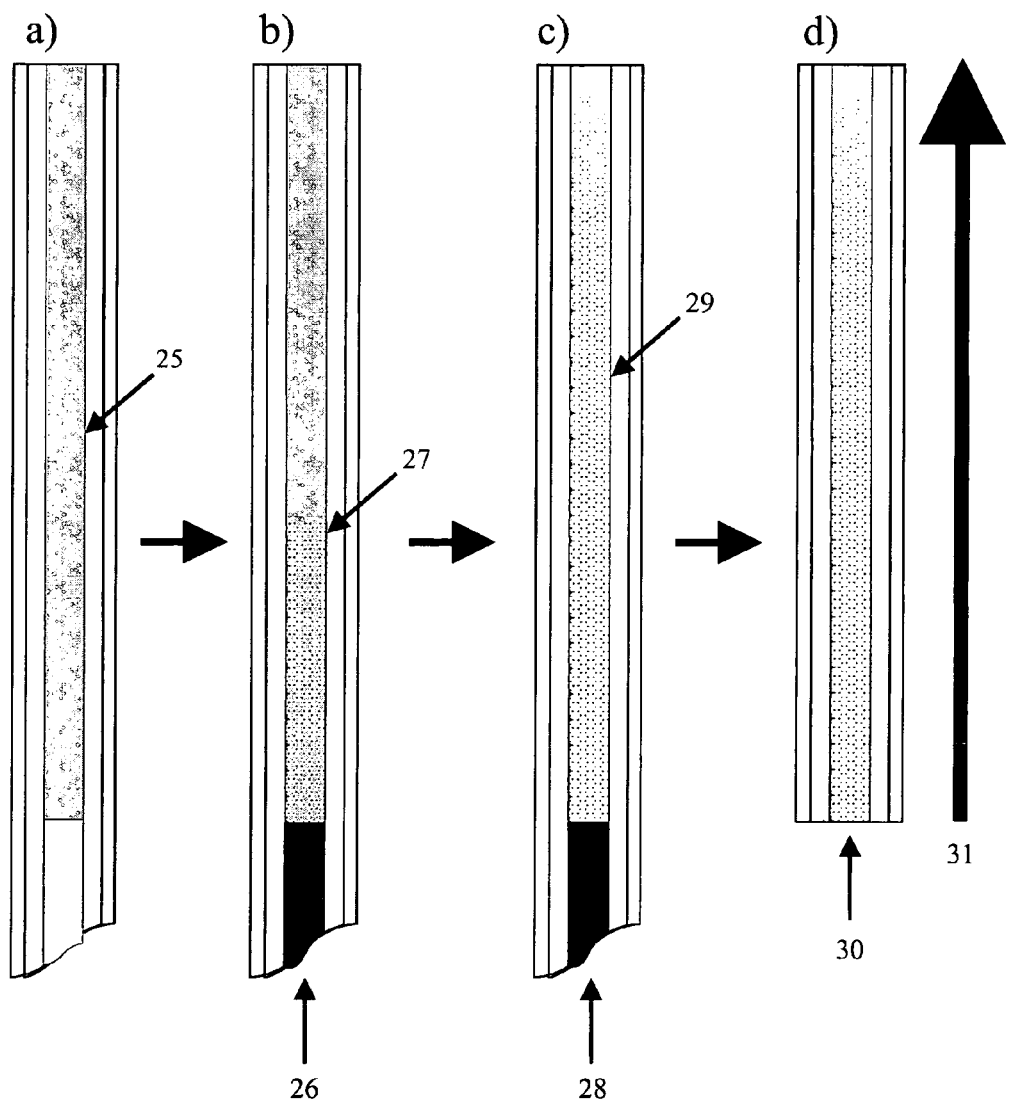
FIG. 3a) to 3d) illustrate a method of producing an inverse colloidal crystal capillary column from a colloidal crystal capillary column made of colloidal crystal particles.
FIG. 3b) shows a housing, which is brought into contact with a precursor for a material of pre-selected index of refraction, a precursor in a solution, a precursor mixture, a precursor mixture in a solution, or a solution of a surface-modifying reagent.
FIG. 3c) shows more liquid infiltration material being supplied wherein the precursor mixture has partially separated into its components with the separation being represented by a gray scale gradient.
FIG. 3d) shows the inverse colloidal crystal column after removal of excess precursor material and removal of the original colloidal crystal template.

FIG. 3 describes the principles of producing the second type of photonic crystal column from the first type of photonic crystal column. The same principle and procedure applies to the manufacture of gradient materials inside capillaries using either the first type of photonic crystal column or the second type of photonic crystal column. A photonic crystal column (25) (which may be the first or second type) is shown in FIG. 3a). In FIG. 3b) the capillary or housing is brought into contact with a precursor (including titanium tetrabutoxide), a precursor solution (tetraethyl orthosilicate or tetramethyl orthosilicate in aqueous hydrochloric acid), a precursor mixture (including silicon tetrabutoxide and titanium tetrabutoxide), a precursor mixture in a solution (including silicon tetrabutoxide and titanium tetrabutoxide in ethanol), or a solution of a surface-modifying reagent (including octadecyltrichlorosilane, perfluoroctyltrichlorosilane) (26).

The mixture or solution is being partially or wholly imbibed, by the photonic crystal column or its inverted form (27). The chemical moieties within the mixtures are separated according to their different physical and chemical properties in a chromatographic process, where the first type (or second type) of photonic crystal column acts as stationary separation phase. The infiltrating material can be imbibed by capillary action or it can be forced into the capillary construct by pressure or it can be infiltrated by applying reduced pressure or applying a vacuum to the open end of the capillary or elongated housing.

In FIG. 3c) more liquid infiltration material is supplied (28) and the precursor mixture has been partially separated into its components (29). The separation is represented by a gray scale gradient. After suitable treatment, possibly including the removal of excess precursor material or the inversion of the original first type of photonic crystal column, the product (30) is obtained, as shown in FIG. 3d). The arrow (31) designates the property gradient, which can be a gradient in such bulk material properties as refractive index and porosity, or a gradient in surface chemistry properties, such as hydrophobicity and bonding selectivity. A refractive index gradient will lead to a gradient of the photonic band structure of the photonic crystal columns.

The inversion process retains the optical quality and photonic band properties of the first type of photonic crystal column, whereas the band gap structure shifts appropriately depending on the inversion material used. The first and second types of photonic crystal columns can be surface modified to tailor their surface properties for specific applications. Since the first type of photonic crystal column structure can be used as a conventional chromatographic stationary phase as discussed hereinafter, the inversion can be conducted in such a fashion that the resulting second type of photonic crystal column possesses a composition gradient along the infiltration axis, as the material mixture used to infiltrate the first type of photonic crystal column can be effectively separated into its constituents due to surface interactions with the first type of photonic crystal column. Since the first and second types of photonic crystal column structures operate as chromatographic stationary phases, the surface modification can be also conducted in such a fashion that the resulting modified first and second types of photonic crystal columns display a gradient in surface properties. The high optical quality of the gradient structures is preserved while the band structure will shift in its spectral position accordingly with the real space position along the gradient.

In contrast to available commercial columns, the periodic dielectric modulation inherent in the photonic crystals columns disclosed herein result in the column having a photonic band structure which interacts with electromagnetic radiation due to the presence of a photonic band structure.

As stated above, the inversion process yields a second photonic crystal column having a second photonic band structure which may be characterized by either a photonic band gap, a stop-band, or combination thereof.

The step of removing the colloidal particles to leave behind an inverted photonic crystal column may include, but is not limited to, exposing the first photonic crystal column to a plasma treatment, thermal treatment, calcination, photocalcination, solvent or acid etching and combinations thereof.

The precursor of the material of selected index of refraction, which is infiltrated into the first photonic crystal column may contain a constituent which, upon reaction of the precursor, produces a solid comprising the constituent itself.

Alternatively, the precursor of the material of selected index of refraction, which is infiltrated into the first photonic crystal column may contain a mixture of constituents, which upon reaction of the precursor, produces a solid comprising a mixture of the constituents. An example is a mixture of bulk titanium tetrabutoxide and bulk zirconium tetrabutoxide. Alternatively, the precursor of the material of selected index of refraction which is infiltrated into the first photonic crystal column may contain a mixture of constituents, which separate from each other in the photonic crystal column as the precursor is flowed into the flow passageways through the photonic crystal column to give a gradient of constituents along the length of the first photonic crystal column, which upon reaction of the precursor, produces a solid comprising a gradient of the several constituents along the length of the resulting second photonic crystal column.

Examples are mixtures of bulk titanium tetrabutoxide and bulk tetramethyl orthosilicate, bulk titanium tetraethoxide and bulk zirconium tetrabutoxide, or bulk titanium tetrabutoxide with polyethylene glycol as porogen.

The selected materials may for example include, but are not limited to, monomeric materials, polymeric materials, organic materials, biomolecular materials, inorganic materials, organometallic materials, metallic materials, nanoparticle materials and mixtures and composites thereof.

Once the first photonic crystal column has been inverted to produce the second column a fluid may be infiltrated into the second column, which contains a solution of a surface-modifying reagent, through the flow passageways through the second colloidal photonic crystal. A reaction is then induced between the surface-modifying reagent and an inner surface of the second photonic crystal material along the length of the second photonic crystal column for modifying the inner surface by etching or chemically and physically immobilizing the reagent. A prominent example is octadecyltrichlorosilane, which reacts with surface hydroxyl groups and is immobilized on the surface to yield "reversed phases" or hydrophobic surfaces.

The solution of the surface-modifying reagent may include one or more surface-modifying reagents which spread or separate from each other in the second photonic crystal column to give a gradient of surface-modifying reagents along the length of the second photonic crystal column. An example is a mixture of alkyltrichlorosilanes with various alkyl chain lengths in solution.

The colloidal crystal capillary columns and the inverse colloidal crystal capillary columns are the basis from which the chromatographic devices are produced in accordance with the present invention. The colloidal crystal capillary columns may serve as conventional chromatographic columns, which are packed with roughly spherical particles several microns in diameter. The inverse colloidal crystal capillary columns are analogous to the more recently developed monolithic columns that now find increasing utilization in separation science and industrial applications. Monolithic columns represent a continuous porous phase where pores and through-pores permeate all of the separation volume.

Interstitial voids, spherical voids or void spaces and through-pores of the colloidal crystal capillary columns and the inverse colloidal crystal capillary column devices can be filled with a mobile phase which can be a gas (including hydrogen, helium, argon, etc.), supercritical gas (including supercritical carbon dioxide), supercritical liquid (water), or a liquid (including methanol, acetonitrile, etc.). As in conventional columns the mobile phase carries a mixture of dissolved chemical moieties (polymers, organic molecules, ions, nano-particles, biomolecules (e.g. proteins for proteomics studies), which is separated into individual components by interaction of the moieties with the separation phase surface of the colloidal crystal capillary columns and the inverse colloidal crystal capillary columns.

The highly uniform structural and optical quality parallel to the long axis of the colloidal crystal capillary columns and the inverted colloidal crystal capillary-based chromatographic columns, allows for an invariant photonic band structure with at least one lower energy stop-band along the radial direction that can be detected and probed in reflection and transmission in selected or combined ranges of the near ultraviolet, visible, or near infrared part of the electromagnetic spectrum.

Since stop-bands shift sensitively with a refractive index change, minute variations of the mobile phase composition inside the chromatographic separation phase are therefore detectable.

In combination with a suitable source of electromagnetic radiation and a detector, the colloidal crystal capillary columns and inverted colloidal crystal capillary columns function as a separation and an inherent detection device. The separation process and mobile phase composition changes, mobile phase containing changing concentrations of analytes and solvent gradients shifting from water or methanol to acetonitrile or mixtures, can be monitored directly at arbitrarily chosen positions in the first or second photonic crystal columns.

Figure 4:
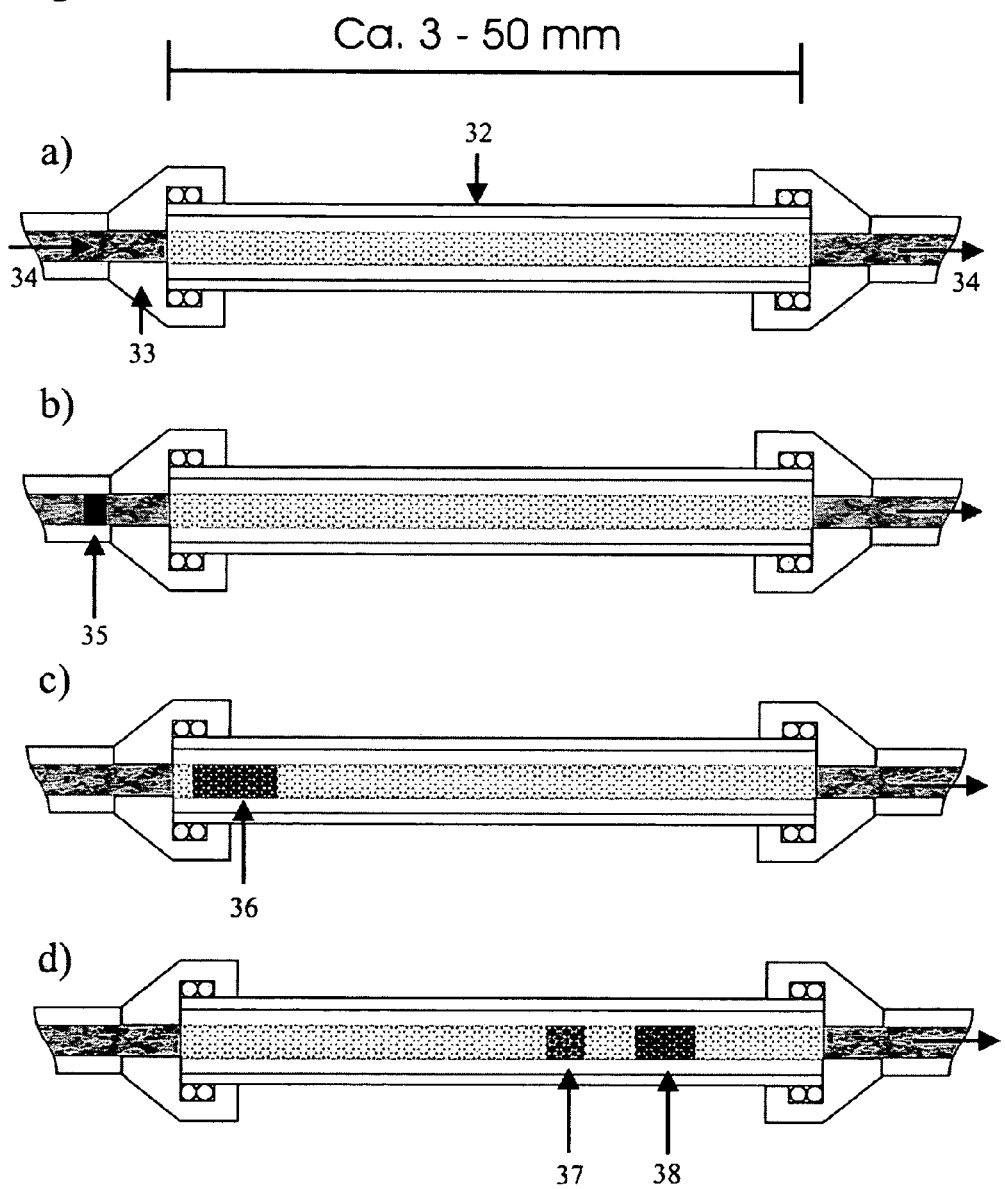
FIGS. 4a) to 4d) illustrate a chromatographic application of the photonic crystal columns and the inverse colloidal crystal columns produced therefrom.
FIG. 4b) shows such a discrete volume of analytes, the black band, shortly before entering the photonic crystal column stationary separation phase.
FIG. 4c) shows the broadening of the analyte band as the chromatographic process begins to separate the individual components.
FIG. 4d) shows that two analytes have been separated and form two distinctive bands as the individual molecular species traverse the photonic crystal column at different speeds due to the unequal surface/stationary phase interaction.

FIGS. 4a) to 4d) illustrate the chromatographic application of the two types of photonic crystal columns. In FIG. 4a) a first photonic crystal column or second photonic crystal column based article (32) is hermetically connected by seals or suitable connectors (33) to a closed system that regulates the flow of a mobile phase or eluent (34), where the mobile phase can be a gas (including hydrogen, helium, argon), supercritical gas (including carbon dioxide), a liquid (including methanol, acetonitrile), or a supercritical liquid (including water). The mobile phase is constantly flowing through the photonic crystal column. The system also provides a possibility to insert discrete volumes of analytes, usually mixtures of molecules or chemical moieties or nano-particles to be separated, into the flowing mobile phase. A black band (35) represents such a discrete volume of analytes shortly before entering the photonic crystal column stationary separation phase (FIG. 4b). FIG. 4c) shows the broadening of the analyte band (36) as the chromatographic process begins to separate the individual components. In FIG. 4d) two analytes (for example two distinct protein molecules) have been separated and form two distinctive bands (37 and 38) as the individual molecular species traverse the photonic crystal column at different speeds due to the unequal surface and stationary phase interaction. The presence of analytes changes the refractive index of the mobile phase. The first and second types of photonic crystal columns optically respond to these changes with a shift of the photonic band structure. These shifts can be detected and accurately measured.

Figure 5:
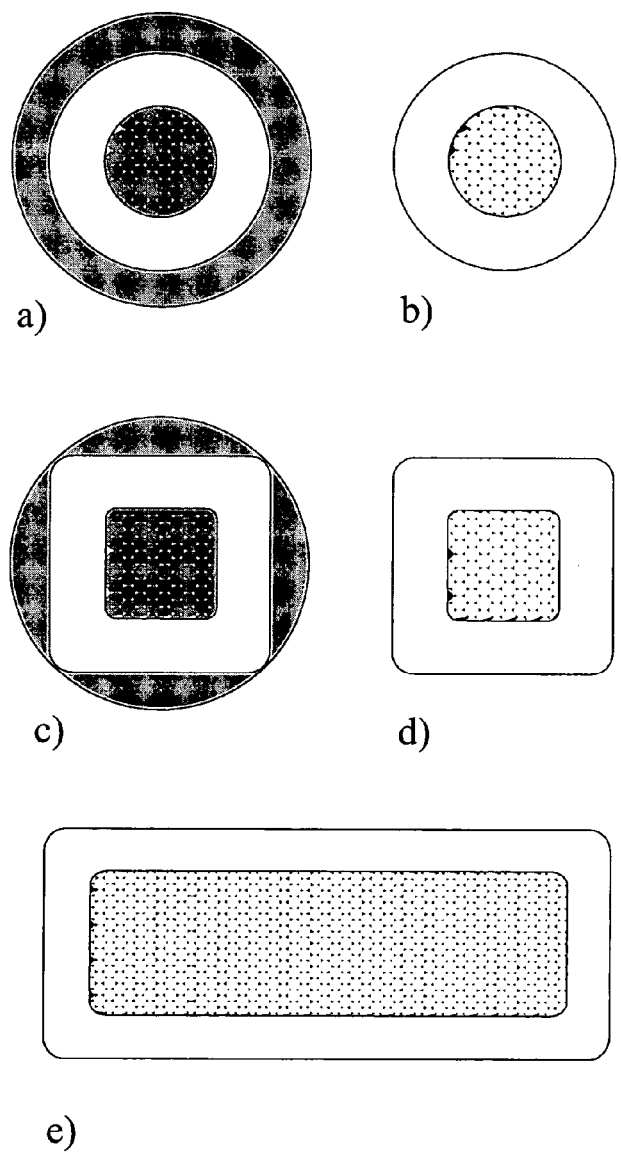
FIGS. 5a) to 5e) show cross sections of typical capillaries and tubes having various cross-sectional shapes, in which photonic crystal columns or their inverted structures can be produced.
FIG. 5b) shows a cross section of an elongated housing or capillary or tubes made out of other materials than that of FIG. 5a)
FIG. 5c) shows a cross-section of a square elongated housing with a tubing coated with a jacket material.
FIG. 5d) shows a cross section of a square elongated housing or capillary or tube made out of other materials than that of FIG. 5c)
FIG. 5e) shows a cross-section of a rectangular elongated housing or capillary or tubing made from various materials.

FIG. 5 displays typical capillaries and tubes having various cross-sectional shapes, which can be filled with the first or second types of photonic crystal columns. FIG. 5a) and 5c) show typical fused silica tubes with round and square cross-sections respectively, which are covered with a jacket polymer material (including polyimide). FIG. 5b) and 5d) are capillaries or tubes made out of other materials (including polymers, glass, metals) also having round and square cross-sections respectively. While round shapes can usually withstand higher pressures, square and rectangular shapes are favored for spectroscopic applications due to the coplanar faces of the capillary. Curvature of the surface of photonic crystals increases the broadening of the band gap displayed by the photonic crystal columns. FIG. 5e) shows a rectangular capillary, which can have high aspect ratios for the different faces and thus yielding thin but wide capillaries ideal for reflectance and transmission spectroscopy. The rectangular capillaries can also be made from a wide range of materials (including glass, fused silica, etc) and can also have a protective jacket material.

Figure 6:
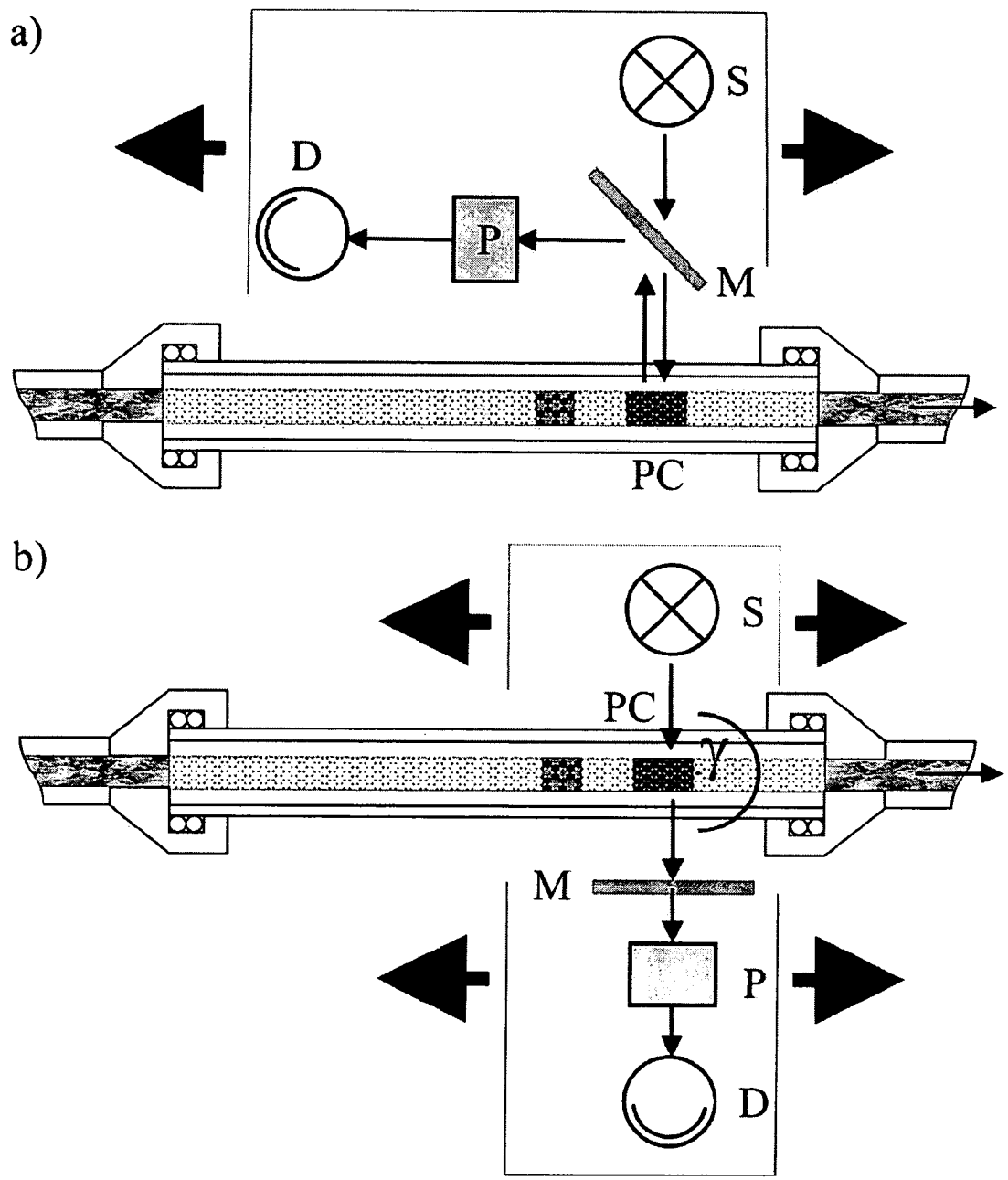
FIG. 6a) shows a chromatographic device using a photonic colloidal crystal column or its inverted structure coupled with an optical system for monitoring the photonic band structure of the photonic columns in reflection as material is separated in the columns.
FIG. 6b) shows a photonic crystal column coupled with another type of optical system for monitoring the photonic band structure of the photonic crystal column in transmission as material is separated in the column.

FIG. 6 shows two modes of monitoring the photonic band structure and shifts therein of the first and second types of photonic crystal columns. A second type of photonic crystal column with a mobile phase (including water, methanol, acetonitrile, hydrogen, carbon dioxide, helium) containing separated analytes (including inorganic, organic, ionic chemical moieties) flowing through the column is given as an example. In FIG. 6a) the second type of photonic crystal column is observed in reflection. Light from a source S, which can be a white light source, an infrared source, or a monochromatic source, etc, passes through a mirror M. The light is then selectively reflected by the photonic crystal inside the capillary. The returning light is then deflected by a mirror M to P. P can be a monochromator, a prism, or a photonic crystal, which spectrally disperse the light. The dispersed light is then detected by a point or an array detector D. Using a dichroic mirror M allows selective monitoring of fluorescence inside the PC, where the fluorescence might be enhanced due to matching fluorescence emission and photonic band structure. In FIG. 6b) the second type of photonic crystal column is observed in transmission. Light from a source S, which can be a white light source, an infrared source, or a monochromatic source, is shone directly on the photonic crystal column. The light is then selectively transmitted by the photonic crystal PC inside the capillary. The second type of photonic crystal column can be exchanged for a first type of photonic crystal column. The transmitted light may pass through a mirror M towards P. P can be a monochromator, a prism, or a photonic crystal, which spectrally disperse the light. The dispersed light is then detected by a point or an array detector D. Using a dichroic mirror M allows selective monitoring of fluorescence inside the PC, where the fluorescence might be enhanced due to matching fluorescence emission and photonic band structure. The fluorescence can stem from fluorescent species dissolved in the mobile phase and/or the analyte mixture, or fluorescent species chemically or physically associated with analytes within the mobile phase or analyte mixture. The fluorescence can also stem from fluorescent species immobilized to the stationary phase.

The bold arrows represent the capability of moving either the experimental set-up or the photonic crystal columns themselves in order to perform the photonic band structure monitoring at arbitrary locations along the capillary axis, if it is necessary.

Figure 7:
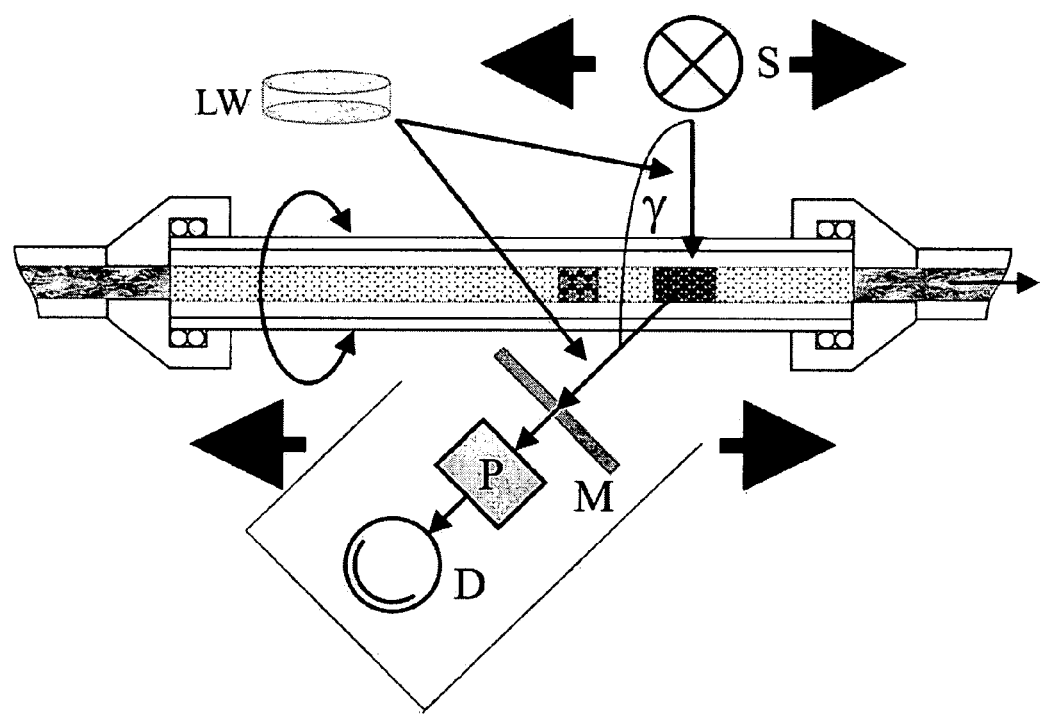
FIG. 7 shows a photonic crystal column similar to FIGS. 6a) and 6b) coupled with another optical system for monitoring the photonic band structure of the photonic crystal column in angular reflection as material is separated in the columns.

FIG. 7 presents the concept of invariance of photonic band structure to rotation of the photonic crystal column around its long capillary axis. For $\gamma=0$ or $180°$ (e.g. reflection or transmission mode, see FIG. 6) the experimental setup can be rotated around the photonic crystal columns or, alternatively, the photonic crystal columns can be rotated themselves. Additionally, a possibility of observing transmission or reflection and other optical phenomena, e.g. fluorescence, in an angular mode is presented (preferably, $\gamma=90°$). Invariance of the photonic band structure to translation along the capillary axis is represented by bold arrows. It shows the capability to either move the experimental set-up or the photonic crystal columns themselves to perform the photonic band structure monitoring at arbitrary locations along the capillary axis. Systems of lenses L and optical fibers W can be introduced into the optical setup to separate the light source and detector D from the photonic crystal column. The letters S, P, D, and M are abbreviations for light source, prism, detector, and mirror, respectively.

FIG. 8 demonstrates two possible modes of monitoring the photonic band structure and shifts therein of the two types of photonic crystal columns. A second type of photonic crystal column with a mobile phase containing separated analytes flowing through is given as an example.

In FIG. 8a) the photonic crystal column is observed in reflection. Light from a source S, which can be a white light source, an infrared source, or a monochromatic source passes through a mirror M. It is then collected and focused by a system of lenses L and can then be coupled into a waveguide or optical fiber W, where another set of focusing lenses can be positioned at the tip of the waveguide The light is then selectively reflected by the photonic crystal PC inside the capillary. The returning light is then collected, focused, guided by LW, and finally deflected by a mirror M to P. P can be a monochromator, a prism, or a photonic crystal, which spectrally disperse the light. The dispersed light is then detected by a point or an array detector D. Using a dichroic mirror M allows selective monitoring of fluorescence inside the PC, where the fluorescence might be enhanced due to matching fluorescence emission and photonic band structure.

In FIG. 8b) the second type of photonic crystal column is observed in transmission. Light from a source S, which can be a white light source, an infrared source, or a monochromatic source, is coupled and decoupled into and out of an optical fiber and guided to the photonic crystal column. Sets of focusing lenses can be positioned at both ends of LW. The light is then selectively transmitted by the photonic crystal inside the capillary. An optical fiber LW collects the transmitted radiation and guides it via a mirror M towards P. A set of focusing lenses may be positioned at both ends of the waveguide. P can be a monochromator, a prism, or a photonic crystal, which spectrally disperse the light. The dispersed light is then detected by a point or an array detector D. Using a dichroic mirror M allows selective monitoring of fluorescence inside the PC, where the fluorescence might be enhanced due to matching fluorescence emission and photonic band structure. The bold arrows represent the capability of moving either the experimental set-up or the photonic crystal columns themselves to perform the photonic band structure monitoring at arbitrary locations along the capillary axis.

Figure 9:
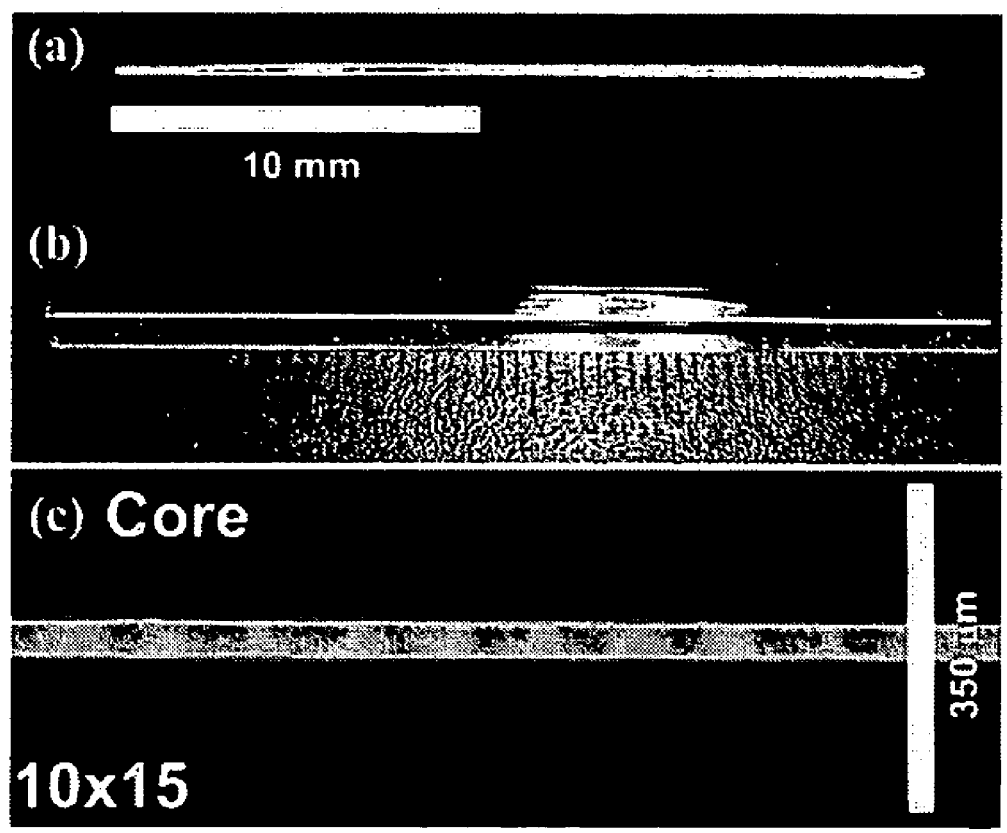
FIG. 9a) shows optical images of a high aspect ratio bare colloidal crystal cylinder with 360 micrometer diameter, assembled by pressure-assisted colloidal microsphere assembly in capillaries (PACMAC) from 225 nanaometer polystyrene microspheres and ejected out of a heavy wall capillary.
FIG. 9b) shows a 360 micrometer inner diameter capillary with a 60 millimeter long capillary colloidal crystal self-assembled inside from 225 nanometer polystyrene microspheres.
FIG. 9c) shows the core of the bare cylinder displaying a homogeneous color band at 10×15 magnification, highly suitable for colloidal crystal chromatography.

FIGS. 9a) to 9c) presents a typical first type of photonic crystal column grown by PACMAC. FIG. 9a) shows optical images of a high aspect ratio bare colloidal crystal cylinder with 360 micrometer diameter, assembled by PACMAC from 225 nanometer polystyrene microspheres and ejected out of heavy wall capillary. The first photonic crystal column made of colloidal crystals displays strong and uniform opalescence. FIG. 9b) represents a 360 micrometer inner diameter capillary with a 60 millimeter long capillary colloidal crystal self-assembled inside from 225 nanometer polystyrene microspheres. The core of the bare cylinder is shown in FIG. 9c) displaying a homogeneous color band at 10×15 magnification, highly suitable for colloidal crystal chromatography.

Figure 10:
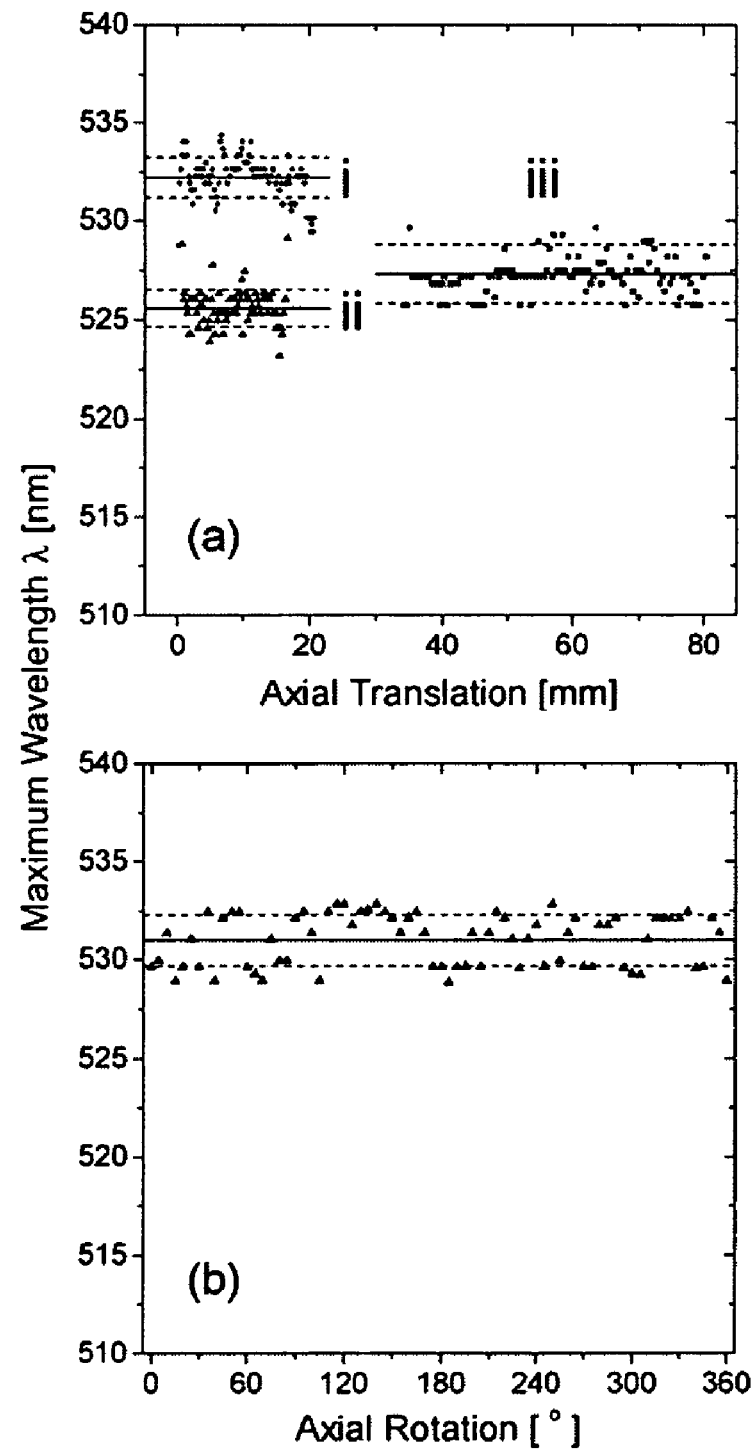
FIGS. 10a) and 10b) show the spectral properties of a colloidal crystal capillary column with 360 micrometer diameter, assembled from 225 nanometer polystyrene microspheres by PACMAC.
FIG. 10b) shows the dependence of the wavelength ($\lambda$) of the stop band maximum of a photonic crystal column having a round cross-section, which displays invariance of reflectivity to rotation around the capillary axis, solid and dashed lines represent mean averages and standard deviations, respectively.

FIG. 10 shows the spectral properties of a colloidal crystal capillary column with 360 micrometer diameter, assembled from 225 nanometer polystyrene microspheres by PACMAC. FIG. 10a) shows the dependence of the wavelength λ of the stop band maximum on axial translation: data sets i and ii from a 21 millimeter-long bare colloidal crystal rod at different focal depths, iii from a 60 millimeter long colloidal crystal inside a heavy wall capillary. The first photonic crystal column construct spectroscopically probed in FIG. 10b) has a round cross-section. Therefore the construct displays invariance of reflectivity to rotation around the capillary axis (data set iii). For all data sets shown here, solid and dashed lines represent mean averages and standard deviations, respectively.

FIG. 10a) shows the dependence of the wavelength λ of the stop band maximum on axial translation: data sets i and ii are taken from a 21 millimeter-long bare colloidal crystal rod at different focal depths, iii is collected from a 60 millimeter long colloidal crystal inside a heavy wall capillary. The photonic crystal column spectroscopically probed in FIG. 10b) has a round cross-section. Therefore the construct displays invariance of reflectivity to rotation around the capillary axis (data set iii). For all data sets shown here, solid and dashed lines represent mean averages and standard deviations, respectively.

Figure 11:
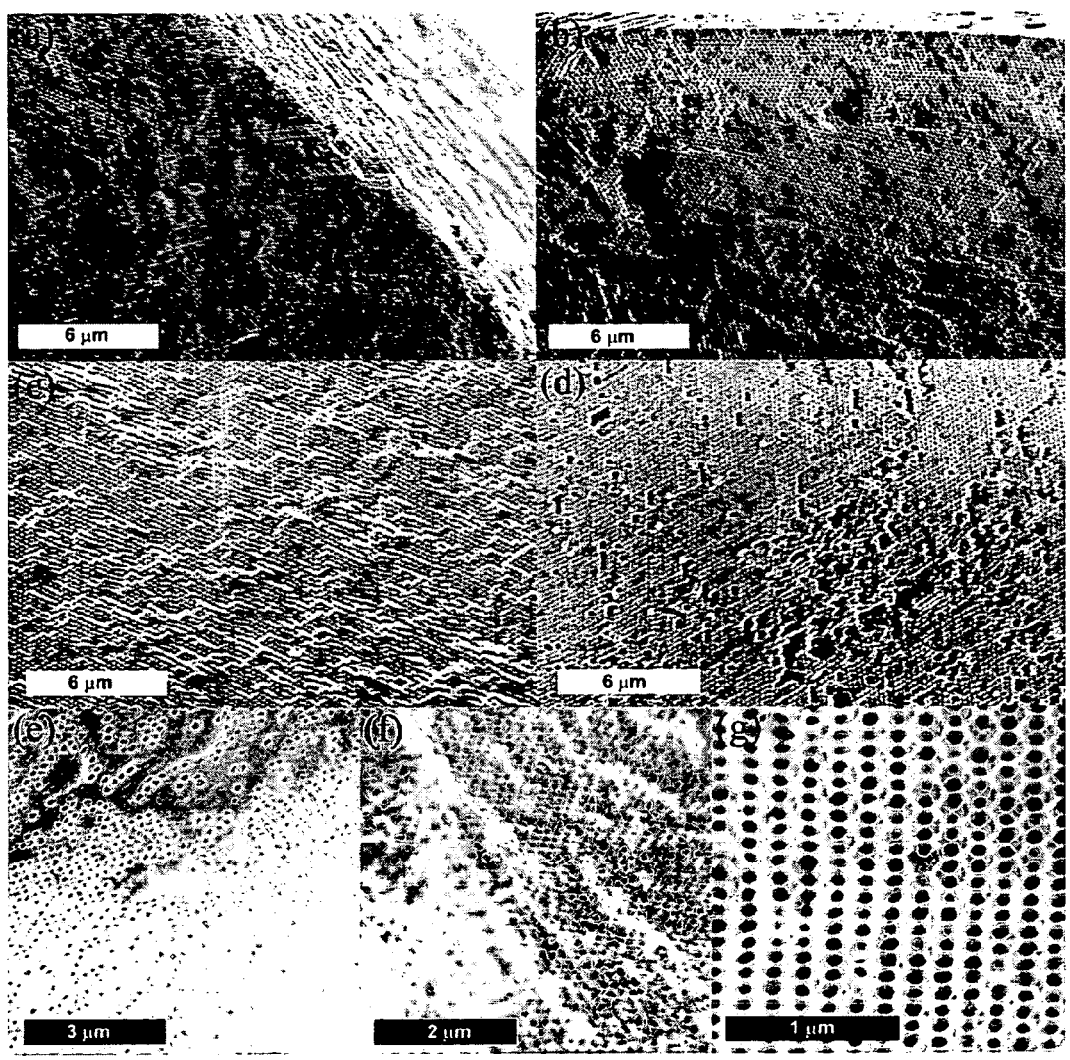
FIGS. 11a) to 11d) show SEM images of a bare colloidal crystal cylinder, self-assembled from 225 nanometer polystyrene microspheres by PACMAC, 11a) shows a cross section of interior surface (edge-on), 11b) cross section with continuous high order in top layers, 11c) cross section of core area, 11d) top view of surface with defects, displaying the {111} plane of a face centered cubic (fcc) colloidal crystal.
FIGS. 11e) to 11g) show inverse silica colloidal crystal cylinders formed in capillaries, 11e) top view of surface, 11f) view from surface into interior (edge-on), 11g) skeleton structure in core area.

FIGS. 11(a-d) shows SEM images of a bare colloidal crystal cylinder, self-assembled from 225 nanometer polystyrene microspheres by PACMAC where FIG. 11a) shows a cross section of interior, surface (edge-on), FIG. 11b) shows a cross section with continuous high order in top layers, FIG. 11c) shows a cross section of core area, FIG. 11d) shows a top view of surface with defects, displaying the {111} plane of an fcc colloidal crystal.

FIGS. 11e) to g) show SEMs of inverse silica colloidal crystal cylinders formed in capillaries where FIG. 11e) is a top view of the surface, FIG. 11f) is a view from surface into interior (edge-on) and FIG. 11g) shows the skeleton structure in the core area.

Figure 12:
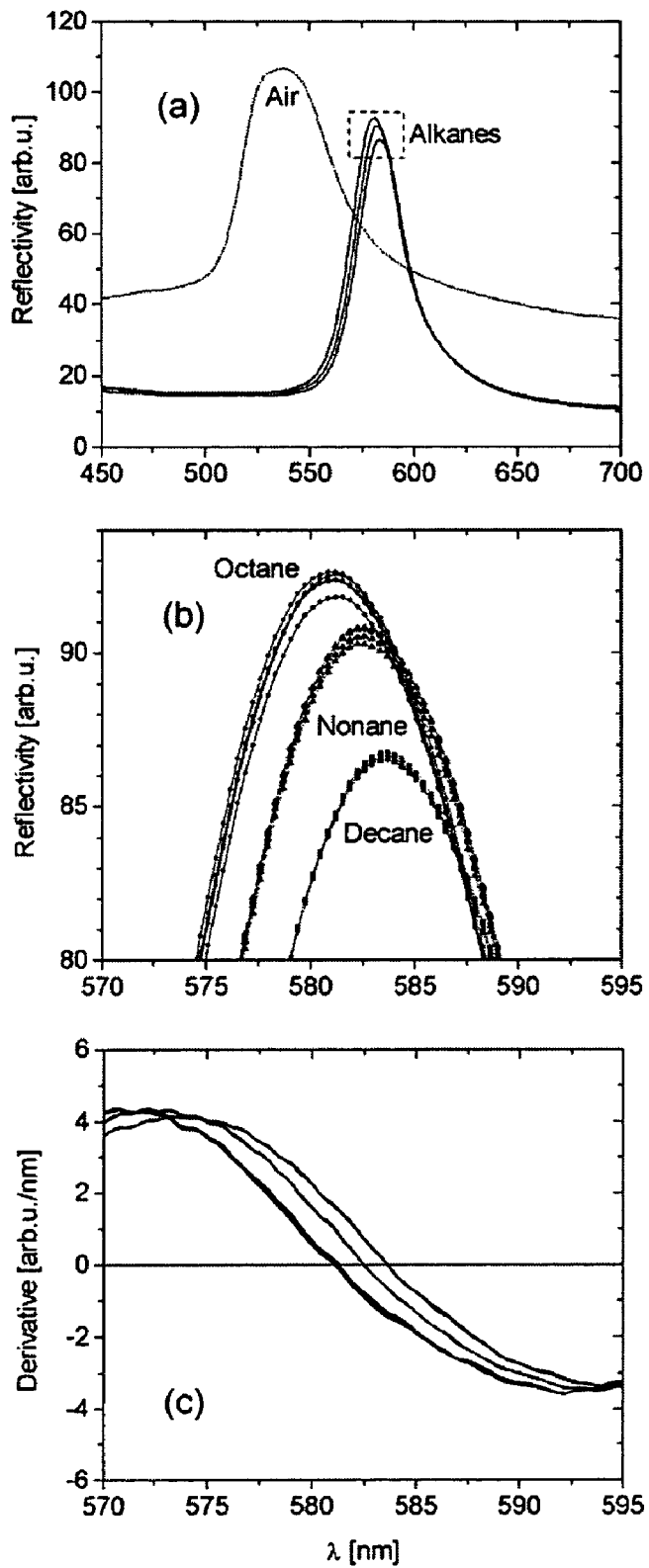
FIGS. 12a) to 12c) show photonic band spectra in reflectance mode of a colloidal crystal capillary column assembled from 225 nanometer polystyrene microspheres by PACMAC inside a heavy wall capillary having 360 micrometer in diameter.
FIG. 12b) shows a zoom-in on the alkane-infiltrated photonic crystal column stop band maxima, with peak wavelengths $\lambda$ for octane 581.2 nm, nonane 582.6 nm, decane 583.7 nm.
FIG. 12c) shows the derivatives of the alkane infiltrated photonic band spectra of a photonic crystal column with the corresponding intercepts at 581.1 nm, 582.4 nm, and 583.5 nm.

FIG. 12 shows photonic band spectra in reflectance mode of a colloidal crystal capillary column assembled from 225 nanometer polystyrene microspheres by PACMAC inside a heavy wall capillary having 360 micrometer in diameter. FIG. 12a) shows the shift of the fundamental stop band, starting with a dry photonic crystal column and progressing by subsequently flowing octane, nonane, and decane through the photonic crystal column. FIG. 12b) shows a zoom-in on alkane-infiltrated photonic crystal column stop band maxima, with peak wavelengths $\lambda$ for octane 581.2 nm, nonane 582.6 nm, decane 583.7 nm. FIG. 12c) shows the derivatives of the alkane infiltrated photonic band spectra of photonic crystal column constructs with the corresponding intercepts at 581.1 nm, 582.4 nm, and 583.5 nm.

FIGS. 13a) and 13b) display structure and optical properties of a photonic crystal column construct in a capillary with a square cross-section. In FIG. 13a) the cross-section of a square capillary is shown. A photonic crystal column has been produced inside the square capillary from 850 nanometer polystyrene microspheres by PACMAC. All faces of the photonic crystal column display the {111} plane of a fcc colloidal crystal. FIG. 13b) shows that the photonic crystal column displays uniform optical behavior in the near infrared over centimeter-long distances. The photonic band structure is nearly invariant to translation along the capillary axis. Thus, the colloidal crystal phases and their inverse constructs display invariant optical properties parallel to the long capillary axis, except for gradient structures where a gradual change in optical properties is expected. First photonic crystal columns and second photonic crystal columns with a circular cross-section display an invariance of optical properties to rotation around the long capillary axis.

Original and modified first photonic crystal columns and second photonic crystal columns are articles, which are functioning according to the same principles as conventional liquid chromatography columns or more recently introduced monolithic columns, respectively. A first photonic crystal column possesses interstitial voids between the microspheres and a second photonic crystal column has a porous morphology based on through-pores and spherical voids with high connectivity to adjacent spherical voids. A major difference between conventional particulate columns and monoliths on the one hand, and first photonic crystal columns and second photonic crystal columns on the other hand is the narrow particle and air-sphere or void-space diameter distribution in first photonic crystal columns and second photonic crystal columns, resulting in long-range order and optical photonic crystal responsiveness due to the regular periodic three-dimensional arrangement of the microspheres or air-spheres. The degree of necking of microspheres in first photonic crystal columns and the pore diameter and the filling fraction of second photonic crystal columns can be precisely controlled by several parameters during the production process.

Depending on the microsphere material (including silica, polystyrene), first photonic crystal columns can be thermally treated, treated with dilute sol-gel precursors (including mixtures of tetraethyl orthosilicate and tetramethyl orthosilicate, water, hydrochloric acid or ammonia), or subjected to chemical vapor deposition (including tetramethyl orthosilicate) to increase the necking between the touching particles. The pore morphology of second photonic crystal columns can be tuned by applying the aforementioned procedures to the original first photonic crystal column template and varying the amount of material infiltrated into the first photonic crystal column, as well as the wettability of an infiltrating liquid or the wettability of the surface of the first photonic crystal column, or using chemical etching (including acid, hydrofluoric acid, solvent, tetrahydrofuran or toluene) of the second photonic crystal column and/or chemical vapor deposition (including tetramethyl orthosilicate) onto the second photonic crystal column after the original first photonic crystal column has been removed.

Certain first photonic crystal columns and second photonic crystal columns can be removed from capillaries either by applying hydrostatic pressure to and ejecting the colloidal crystal phase from capillaries or by dissolution or other physical and chemical means of removal of the capillary or elongated housing material, including acid (hydrofluoric acid) or solvent etching of the housing material. These free-standing first photonic crystal columns and second photonic crystal columns are called ejected first photonic crystal columns and ejected second photonic crystal columns, respectively.

The first photonic crystal columns, second photonic crystal columns, ejected first photonic crystal columns, and ejected second photonic crystal columns may be utilized as stationary phases for filtering, separation processes, and for various chromatographic applications.

A liquid mobile phase can flow through the monolithic first photonic crystal columns, second photonic crystal columns, ejected first photonic crystal columns, and ejected second photonic crystal columns under pressure, where the ejected first photonic crystal columns and ejected second photonic crystal columns have to be transferred into a suitable chromatographic tube material, where the ejected first photonic crystal columns and ejected second photonic crystal columns act as exchangeable separation phase cartridges. All the above mentioned photonic crystal column constructs can also be utilized in a chromatographic process comparable to thin layer chromatography where the mobile phase is propelled by capillary forces generated within the material without applying pressure. Free-standing constructs do not need to be encased for this particular application. Mixtures of chemical moieties dissolved in the mobile phase are separated according to their chemical and physical properties, as they interact with the surface of the constructs or all of the separation phase. The chemical moieties, which can be separated, include but are not limited to charged, organic, inorganic, macromolecular and biological (synthetic and natural) molecules, polymers, proteins, DNA strands, ions, complexes, nano-particles, and quantum dots and particles.

Second photonic crystal columns and their modified variants, operating similar to commercial monolithic columns, drastically reduce the back pressure experienced by the mobile phase inside the stationary phase due to the high connectivity of the spherical voids and the low filling fraction (<24%). At the same time, they offer a very high surface area advantageous for the separation. The superior structural order of first photonic crystal columns and second photonic crystal columns due to the low polydispersity and ordered close-packing of the colloidal spheres used in their construction reduces the broadening of the analyte distribution as the mobile phase traverses the voids.

Due to the reduced column dimensions, their required lengths will also be reduced to a few millimeters, which will in turn decrease the spreading of the separated chemical moieties by various diffusion processes as the dwelling time inside the column is also minimized. Additionally, shorter columns will reduce the back pressure.

Second photonic crystal columns and their modified descendants used in chromatographic columns as disclosed herein advantageously are fritless, which means that these columns do not require a mechanical support to contain the particulate material constituting the separation medium. Frits are an additional source of analyte spreading and diffusion during chromatographic separation. Overall, these constructs are highly efficient separation media, which offer shorter analysis times, a decrease in solvent consumption and thus are capable of rendering chromatographic setups based on first photonic crystal columns and second photonic crystal columns much more cost efficient.

First photonic crystal columns, second photonic crystal columns, ejected first photonic crystal columns, and ejected second photonic crystal columns are intrinsic devices since these constructs by virtue of being colloidal photonic crystals have inherent detection capabilities with applications not necessarily limited to the chromatographic processes. The colloidal crystal phases and their inverse constructs display a photonic band structure, comprising higher energy bands and at least one lower energy stop-band. The spectral position of features in the band structure depends on the sphere dimensions, sphere material, and the necking properties in first photonic crystal columns, material and filling fraction of interstitial voids in second photonic crystal columns. It is the refractive index contrast, next to the air sphere diameter and the filling fraction of the wall material, between the constituent materials of first photonic crystal column and second photonic crystal column that governs the spectral position and features of the photonic band structure. The band structure will shift upon changes in the refractive index of the mobile phase inside a photonic crystal column. As a result, a change of the refractive index of the mobile phase, due to a change of the composition of the mobile phase constituents or due to the presence of dissolved chemical moieties, will cause an optical response that can be monitored spectroscopically. Therefore, it is possible to detect solvent gradients, or separated analytes, and effectively monitor the separation process. The response to the refractive index changes of the separated media inside first photonic crystal columns, second photonic crystal columns, ejected first photonic crystal columns, or ejected second photonic crystal columns is essentially instantaneous.

The band structure shifts due to refractive index changes of first photonic crystal column, second photonic crystal columns, ejected first photonic crystal columns, and ejected second photonic crystal columns are usually rather small but can be reliably detected by virtue of their high structural and optical quality by using a spectroscopic setup with appropriate sensitivity. Spectral shifts can be continuously measured and monitored by analyzing the reflection and/or transmission spectra directly or by generating the first derivative of the spectra and determining corresponding zero-intercept positions.

Spectral dependence of the optical properties on mobile phase composition can be recorded both in transmission and reflection, where the light source and the detector are either positioned on opposite sides or the same side of the first photonic crystal columns, second photonic crystal columns, ejected first photonic crystal columns, or ejected second photonic crystal columns. Light sources can be polychromatic or monochromatic, the light can be directly shone on the column, focused on the stationary phase by a system of lenses or objectives, or guided to the column by fiber optical waveguides. The light can also be sampled and directed to the detector using a system of lenses or fiber optics. The sampled light can be spectrally dispersed by a monochromator, prism, or photonic crystal and detected by a point detector (e.g. pin photodiode, avalanche photodiode, photomultiplier) or an array detector (e.g. CCD-camera, diode array).

Due to the photonic crystal nature of the stationary phase it is also possible to monitor photoluminescence, phosphorescence, or fluorescence from light emitting sources either dissolved in the mobile phase or immobilized onto the surface of the separation phase. The light absorbing and emitting characteristics of these internal light sources can be tuned to the features of interest in the photonic band structure of the first photonic crystal column, second photonic crystal column, ejected first photonic crystal column, or ejected second photonic crystal columns or vice versa to improve light emission and enhance the optical signal collected.

The light-emitting sources are fluorescent or photoluminescent molecules or quantum dots that can physically or chemically bind to a specific or several specific analytes in the mobile phase. Upon such bonding, the frequency of the light emission is shifted to match the features in the photonic band structure of the first photonic crystal columns, second photonic crystal columns, ejected first photonic crystal columns, or ejected second photonic crystal columns in a specific fashion or the light emission intensity is altered (e.g. completely or partially quenched). In combination with the photonic stationary phases of the first photonic crystal columns, second photonic crystal columns, ejected first photonic crystal columns, or ejected second photonic crystal columns the presence of analytes in separated mixtures can be detected by monitoring the details of the light emission of these internal probes in time.

In an analogous fashion, probes with surface plasmon states that are capable of changing in the presence of certain analytes can be integrated in the first photonic crystal columns, second photonic crystal columns, ejected first photonic crystal columns, or ejected second photonic crystal columns. Photon-plasmon interaction can also be tailored to the band structure of the photonic crystal columns and will result in dramatic changes like optical amplification of signals during analyte separation and detection.

High structural quality of a first photonic crystal column, second photonic crystal column, ejected first photonic crystal column, and ejected second photonic crystal column results in reproducible and stable optical responses, which are invariant to translation parallel to the long axis of the respective capillary and in the case of capillaries with circular cross-section to rotation, so that spectral monitoring can be conveniently conducted at arbitrary positions on the constructs.

The photonic crystal columns, described herein are not based on hydrogels. The chromatographic photonic crystal columns disclosed herein separate species in the fluids flowing therethrough by molecule-surface interaction and/or molecule pore interaction and not by entropic trapping. While in another invention by Asher (see Hydrogels with crystalline colloidal array of water voids for macromolecule separations and detection. Asher, Sanford A.; Liu, Lei. (University of Pittsburgh, USA). PCT Int. Appl. (2000), 48 pp. CODEN: PIXXD2 WO 2000000278 A1 20000106; Liu L., Li P., Asher S. A. Entropic trapping of macromolecules by mesoscopic periodic voids in a polymer hydrogel. Nature (1999 Jan. 14), 397(6715), 141-4) the molecules to be separated have to permeate through the hydrogel to the water voids, all mass transport in the present invention is achieved by a continuous mobile phase motion through the interstitial voids or connecting pores. Open mesopores enhance the separation but do not participate in the mass transfer.

The current invention also avoids the problems associated with hydrogel swelling, which would interfere with the monitoring of the spectral properties. The void and pore dimensions in the described photonic crystal columns are invariant to solvent and temperature changes. A swelling of the colloidal crystal separation phase causes a change of the lattice parameters of the photonic crystal and also the filling fraction, which ultimately will lead to a shift of the band structure. These problems do not arise in the here presented invention as the spheres or wall materials do not react physically or chemically with the mobile phase. Analytes also do not react physically or chemically with the stationary phase, except in the case of specific chemical moieties immobilized on the separation phase surface intended to interact with analytes.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A chromatographic separation medium, comprising:
an elongated housing containing a photonic crystal column enclosed therein having a photonic band structure which interacts with electromagnetic radiation along a length of the photonic crystal column, the photonic crystal column including interconnected voids defining flow passageways through the photonic crystal column for a liquid, gaseous, critical, or supercritical mobile phase containing materials to be separated by the photonic crystal column, wherein changes in the photonic band structure of the photonic crystal column occur as the liquid, gaseous, critical, or supercritical mobile phase containing materials to be separated is flowed through said photonic crystal column and separated therein.

2. The chromatographic separation medium according to claim 1 wherein said photonic band structure includes one of a photonic band gap, a stop-band, and combinations thereof.

3. The chromatographic separation medium according to claim 2 wherein said changes in the photonic band structure of the photonic crystal column as a liquid, gaseous, critical, or supercritical mobile phase containing materials to be separated is flowed through said photonic crystal column and separated therein include changes in the photonic band structure upon changes in refractive index of the mobile phase traveling through the photonic crystal column, which cause a shift in a wavelength of optical diffraction along the length of the photonic crystal that can be monitored spectroscopically.

4. The chromatographic separation medium according to claim 3 wherein the changes in the refractive index of the mobile phase arises due to a change of the composition of the mobile phase constituents or due to the presence of dissolved chemical moieties.

5. The chromatographic separation medium according to claim 2 wherein said photonic band structure displays a photonic band gap which can be detected either in reflection or transmission or in combinations thereof in an ultraviolet, visible, near infrared, and/or infrared region of the electromagnetic spectrum.

6. The chromatographic separation medium according to claim 2 wherein the photonic crystal column includes a packed array of colloidal crystal particles defining an elongated photonic crystal, wherein the interconnected voids are spaces between the colloidal crystal particles.

7. The chromatographic separation medium according to claim 6 wherein the colloidal crystal particles are substantially monodisperse colloidal microspheres.

8. The chromatographic separation medium according to claim 7 wherein said substantially monodisperse colloidal microspheres have diameters in a range from about 50 nanometers to about 3 micrometers.

9. The chromatographic separation medium according to claim 7 wherein said substantially monodisperse colloidal microspheres are made of a solid or gel material.

10. The chromatographic separation medium according to claim 7 wherein said substantially monodisperse colloidal microspheres are porous with different pore sizes in a range from Ångstroms to an order of micrometers.

11. The chromatographic separation medium according to claim 7 wherein said substantially monodisperse colloidal microspheres are porous with ordered monodisperse pores with pore sizes in a range from Ångstroms to an order of micrometers.

12. The chromatographic separation medium according to claim 7 wherein said substantially monodisperse colloidal microspheres are made of a material selected from the group consisting of ceramics, silica, titania, zirconia, alumina, magnesia, oxides, chalcogenides, borides, carbides, pnictides, silicides, metals, polymers, nano-crystals, composites of said aforesaid materials and spherical core-shell particles made of combinations of said aforesaid materials.

13. The chromatographic separation medium according to claim 12 wherein said polymers are selected from the group consisting of non-cross-linked and cross-linked polystyrene, polymethacrylates, polyacrylates, polyurethanes, polyketones, polyethers, polyvinyl, polybutadiene, inorganic polymers, metallopolymers, copolymers, grafted polymers, block-copolymers, dendrimers, biopolymers, and composites of the aforesaid polymer materials.

14. The chromatographic separation medium according to claim 7 wherein said substantially monodisperse colloidal microspheres each have a surface, which is modified by one of plasma treatment in the presence of reactive or non-reactive gases, and by chemical agents including physically or chemically surface-immobilizing said agents selected from the group consisting of etching agents, hydrophobic agents, charge-altering and carrying agents, functional group carrying agents, surface-active molecules, biomolecular agents, nanoclusters and polyelectrolytes.

15. The chromatographic separation medium according to claim 2 wherein the elongated housing is made of a material which is transparent or partially transparent material in ultra-violet, visible, near infrared and infrared spectral regions of the electromagnetic spectrum.

16. The chromatographic separation medium according to claim 15 wherein the elongated housing is made of a material selected from the group consisting of polymers, oxides, chalcogenides, glasses, metals and semiconductors, combinations and composites of the aforesaid materials.

17. The chromatographic separation medium according to claim 2 wherein the elongated housing is porous.

18. The chromatographic separation medium according to claim 17 wherein said porous elongated housing has pores with different pore sizes in a range from Ångstroms to an order of micrometers.

19. The chromatographic separation medium according to claim 17 wherein said porous elongated housing has ordered monodisperse pores with pore sizes in a range from Ångstroms to an order of micrometers.

20. The chromatographic separation medium according to claim 2 wherein the elongated housing includes chemical surface patterns on an interior surface of the elongated housing.

21. The chromatographic separation medium according to claim 2 wherein the elongated housing includes relief surface patterns on an interior surface of the elongated housing.

22. The chromatographic separation medium according to claim 2 wherein the elongated housing is rigid or flexible.

23. The chromatographic separation medium according to claim 5 integrated as part of a chromatography apparatus including an optical system optically coupled to said photonic crystal column for monitoring changes in the photonic band structure of the photonic crystal column as a liquid, gaseous, critical, or supercritical mobile phase containing materials to be separated is flowed through said photonic crystal column and separated therein.

24. The chromatographic separation medium according to claim 23 wherein said optical system optically coupled to said photonic crystal column includes a light source, directing and focusing optics for guiding a beam of light from said light source to said photonic crystal column and from said photonic crystal column in reflectance or transmission mode to a light analysis means for spectrally dispersing the light after interaction of the light beam with the photonic crystal column, and a detection means for detecting said dispersed light.

25. The chromatographic separation medium according to claim 24 including a gantry to which the optical system is attached for moving said optical system along a length of said elongated housing containing the photonic crystal column.

26. The chromatographic separation medium according to claim 24 wherein said light analysis means is one of a monochromator, a grating, a prism, and a photonic crystal, which spectrally disperses the light.

27. The chromatographic separation medium according to claim 24 wherein said detection means is a point detector or an array detector.

28. The chromatographic separation medium according to claim 1 wherein the photonic crystal column is an inverted packed array of colloidal crystal particles defining an elongated photonic crystal having interconnected void spaces between the colloidal crystal particles, wherein a material of pre-selected index of refraction is infiltrated into the interconnected void spaces and the colloidal crystal particles are removed forming second interconnected air voids thereby leaving behind a second photonic crystal column comprised of the material of pre-selected index of refraction and the second interconnected air voids, the second colloidal photonic crystal column having substantially uniform optical properties along a length of the column having a second photonic band structure which interacts with electromagnetic radiation along a length of the photonic crystal, and the second interconnected air voids defining second flow passageways through said material of pre-selected index of refraction for a liquid, gaseous, critical, or supercritical mobile phase containing materials to be separated by the second photonic crystal column.

29. The chromatographic separation medium according to claim 28 wherein said second photonic band structure includes one of a photonic band gap, a stop-band, and combinations thereof.

30. The chromatographic separation medium according to claim 29 wherein changes are induced in the second photonic band structure of the second photonic crystal column as a liquid, gaseous, critical, or supercritical mobile phase containing materials to be separated is flowed through said second photonic crystal column and separated therein include changes in the second photonic band structure upon changes in the refractive index of the mobile phase traveling through the second photonic crystal column, which cause a shift in a wavelength of optical diffraction along the length of the second photonic crystal that can be monitored spectroscopically.

31. The chromatographic separation medium according to claim 29 wherein the interconnected air voids are substantially monodisperse.

32. The chromatographic separation medium according to claim 31 wherein the substantially monodisperse air voids have diameters in a range from about 50 nanometers to about 3 micrometers.

33. The chromatographic separation medium according to claim 29 wherein said material of pre-selected index of refraction is a solid or gel material.

34. The chromatographic separation medium according to claim 29 wherein said material of pre-selected index of refraction is porous with different pore sizes in a range from Ångstroms to an order of micrometers.

35. The chromatographic separation medium according to claim 29 wherein said material of pre-selected index of refraction is porous having ordered monodisperse pores with pore sizes in a range from Ångstroms to an order of micrometers.

36. The chromatographic separation medium according to claim 29 wherein an interior surface of said material of pre-selected index of refraction, in which the air voids are embedded, is modified by one of plasma treatment in the presence of reactive or non-reactive gases, and chemical agents including physically or chemically surface-immobilizing said agents selected from the group consisting of etching agents, hydrophobic agents, charge-altering and carrying agents, functional group carrying agents, surface-active molecules, biomolecular agents, nanoclusters and polyelectrolytes.

37. The chromatographic separation medium according to claim 29 wherein said material of pre-selected index of refraction is selected from the group consisting of ceramics, silica, titania, zirconia, alumina, magnesia, oxides, chalcogenides, borides, carbides, pnictides, silicides, metals, polymers, nano-crystals and composites of the aforesaid materials.

38. The chromatographic separation medium according to claim 37 wherein said polymers are selected from the group consisting of cross-linked and non cross-linked polystyrene, polymethacrylates, polyacrylates, polyurethanes, polyketones, polyethers, polyvinyl, polybutadiene, inorganic polymers, metallopolymers, copolymers, grafted polymers, block-copolymers, dendrimers, biopolymers, and composites of the aforesaid polymer materials.

39. The chromatographic separation medium according to claim 29 wherein the elongated housing is made of a material which is transparent or partially transparent in ultra-violet, visible, near infrared and infrared spectral regions of the electromagnetic spectrum.

40. The chromatographic separation medium according to claim 39 wherein the elongated housing is made of a material selected from the group consisting of polymers, oxides, chalcogenides, glasses, metals and semiconductors, combinations and composites of the aforesaid materials.

41. The chromatographic separation medium according to claim 29 wherein the elongated housing is porous.

42. The chromatographic separation medium according to claim 41 wherein said porous elongated housing has pores with different pore sizes in a range from Ångstroms to an order of micrometers.

43. The chromatographic separation medium according to claim 41 wherein said porous elongated housing has ordered monodisperse pores with pore sizes in a range from Ångstroms to an order of micrometers.

44. The chromatographic separation medium according to claim 29 wherein the elongated housing includes chemical surface patterns on an interior surface of the elongated housing.

45. The chromatographic separation medium according to claim 29 wherein the elongated housing includes relief surface patterns on an interior surface of the elongated housing.

46. The chromatographic separation medium according to claim 29 wherein the elongated housing is rigid or flexible.

47. The chromatographic separation medium according to claim 30 integrated as part of a chromatographic apparatus including an optical system optically coupled to said photonic crystal column for monitoring changes in the photonic band structure of the photonic crystal column as a liquid, gaseous, critical, or supercritical mobile phase containing materials to be separated is flowed through said second photonic crystal column and separated therein.

48. The chromatographic separation medium according to claim 47 wherein said optical system optically coupled to said photonic crystal column includes a light source, directing and focusing optics for guiding a beam of light from said light source to said photonic crystal column and from said photonic crystal column in reflectance or transmission mode to a light analysis means for spectrally dispersing the light after interaction of the light beam with the photonic crystal column, and a detection means for detecting said dispersed light.

49. The chromatographic separation medium according to claim 48 including a gantry to which the optical system is attached for moving said optical system along a length of said elongated housing containing the photonic crystal column.

50. The chromatographic separation medium according to claim 48 wherein said light analysis means is one of a monochromator, a grating, a prism, and a photonic crystal, which spectrally disperses the light.

51. The chromatographic separation medium according to claim 48 wherein said detection means is a point detector or an array detector.

52. A chromatographic method, comprising the steps of:
flowing a liquid, gaseous, critical, or supercritical mobile phase containing materials to be separated through a chromatographic separation medium which includes a photonic crystal column, the photonic crystal column having a photonic band structure which interacts with electromagnetic radiation along a length of the photonic crystal column, the photonic crystal column including interconnected voids defining flow passageways therethrough, wherein changes in the photonic band structure of the photonic crystal column occur as the liquid, gaseous, critical, or supercritical mobile phase containing materials to be separated is flowed through said photonic crystal column and separated therein; and
spectroscopically monitoring for changes in the photonic band structure of the photonic crystal column as the liquid, gaseous, critical, or supercritical mobile phase flows through the photonic crystal column and correlating any changes in the photonic band structure with the materials being separated.

53. The chromatographic method according to claim 52 wherein said photonic band structure includes one of a photonic band gap, a stop-band, and combinations thereof.

54. The chromatographic method according to claim 52 wherein said changes in the photonic band structure of the photonic crystal column as a liquid, gaseous, critical, or supercritical mobile phase containing materials to be separated is flowed through said photonic crystal column and separated therein include changes in the photonic band structure upon changes in refractive index of the mobile phase traveling through the photonic crystal column, which cause a shift in a wavelength of optical diffraction along the length of the photonic crystal that can be monitored spectroscopically, and wherein the changes in the refractive index of the mobile phase arises due to a change of the composition of the mobile phase constituents or due to the presence of dissolved chemical moieties.

55. The chromatographic method according to claim 52 wherein the photonic crystal column includes an array of packed colloidal crystal particles defining an elongated photonic crystal inside an elongated housing, wherein the interconnected voids are spaces between the packed colloidal crystal particles forming flow passageways through said packed colloidal crystal particles for a liquid, gaseous, critical, or supercritical mobile phase containing materials to be separated by the photonic crystal column.

56. The chromatographic method according to claim 55 wherein the colloidal photonic crystal column is removed from the elongated housing to form a free-standing colloidal photonic crystal column.

57. The chromatographic method according claim 52 wherein the photonic crystal column includes an array of packed colloidal crystal particles defining an elongated photonic crystal, including a gradient of one or more surface-modifying reagent components along a length of the photonic crystal column wherein the interconnected voids are spaces between the packed colloidal crystal particles forming flow passageways through said photonic crystal column for a liquid, gaseous, critical, or supercritical mobile phase containing materials to be separated by the surface gradient photonic crystal column.

58. The chromatographic method according to claim 57 wherein the colloidal photonic crystal column is removed from the elongated housing to form a free-standing colloidal photonic crystal column.

59. The chromatographic method according to claim 55 wherein the colloidal crystal particles are substantially monodisperse colloidal microspheres.

60. The chromatographic method according to claim 59 wherein said substantially monodisperse colloidal microspheres have diameters in a range from about 50 nanometers to about 3 micrometers.

61. The chromatographic method according to claim 59 wherein said substantially monodisperse colloidal microspheres are made of a solid or gel material.

62. The chromatographic method according to claim 59 wherein said substantially monodisperse colloidal microspheres are porous with different pore sizes in a range from Ångstroms to an order of micrometers.

63. The chromatographic method according to claim 59 wherein said substantially monodisperse colloidal microspheres are porous with ordered monodisperse pores with pore sizes in a range from Ångstroms to an order of micrometers.

64. The chromatographic method according to claim 59 wherein said colloidal particles are consolidated by any one or combination of thermal sintering, hydrothermal treatment and chemical vapour deposition to cause, or increase necking of the colloidal particles.

65. The chromatographic method according to claim 59 wherein said substantially monodisperse colloidal microspheres are made of a material selected from the group consisting of ceramics, silica, titania, zirconia, alumina, magnesia, oxides, chalcogenides, borides, carbides, pnictides, silicides, metals, polymers, nano-crystals, composites of aforesaid materials and spherical core-shell particles made of combinations of the aforesaid materials.

66. The chromatographic method according to claim 65 wherein said polymers are selected from the group consisting of non-cross-linked and cross-linked polystyrene, polymethacrylates, polyurethanes, polyketones, polyethers, polyvinyl, polybutadiene, inorganic polymers, metallopolymers, copolymers, grafted polymers, block-copolymers, dendrimers, biopolymers, and composites of the aforesaid polymer materials.

67. The chromatographic method according to claim 59 wherein said substantially monodisperse colloidal microspheres each having a surface, which is modified by one of plasma treatment in the presence of reactive or non-reactive gases, and chemical agents including physically or chemically surface-immobilizing said agents selected from the group consisting of etching agents, hydrophobic agents, charge-altering and carrying agents, functional group carrying agents, surface-active molecules, biomolecular agents, nanoclusters and polyelectrolytes.

68. The chromatographic method according to claim 55 wherein the colloidal photonic crystal column has a length in a range from micrometers to meters.

69. The chromatographic method according to claim 55 wherein the elongated housing is made of a material which is optically transparent or partially transparent material in the ultra-violet, visible, near infrared and infrared spectral regions.

70. The chromatographic method according to claim 69 wherein the elongated housing is rigid or flexible.

71. The chromatographic method according to claim 69 wherein the elongated housing has an inner cross-section which is one of square, rectangular, triangular, hexagonal, elliptical and circular, and wherein the inner cross-section has dimensions in a range from about 10 micrometers to several centimeters.

72. The chromatographic method according to claim 69 wherein the elongated housing is porous.

73. The chromatographic method according to claim 72 wherein said porous elongated housing has pores with different pore sizes in a range from Ångstroms to an order of micrometers.

74. The chromatographic method according to claim 72 wherein said porous elongated housing has ordered monodisperse pores with pore sizes in a range from Ångstroms to an order of micrometers.

75. The chromatographic method according to claim 71 wherein the elongated housing includes chemical surface patterns on the interior surface of the elongated housing.

76. The chromatographic method according to claim 71 wherein the elongated housing includes relief surface patterns on the interior surface of the elongated housing.

77. The chromatographic method according to claim 71 wherein the elongated housing is made of a material selected from the group consisting of polymers, oxides, chalcogenides, glasses, metals and semiconductors combinations and composites of aforesaid materials.

78. The chromatographic method according to claim 52 wherein the step of spectroscopically monitoring for changes in the photonic band structure of the photonic crystal column includes coupling an optical system to said photonic crystal column for monitoring changes in the photonic band structure of the photonic crystal column, wherein said optical system includes a light source, directing and focusing optics for guiding a beam of light from said light source to said photonic crystal column and from said photonic crystal column in reflectance or transmission mode to a light analysis means for spectrally dispersing the light after interaction of the light beam with the photonic crystal column, and detection means for detecting said dispersed light.

79. The chromatographic method according to claim 78 including moving the optical system along a length of said photonic crystal column.

80. The chromatographic method according to claim 78 wherein said changes in the photonic band structure of the photonic crystal column as a liquid, gaseous, critical, or supercritical mobile phase containing materials to be separated is flowed through said photonic crystal column and separated therein include changes in the photonic band structure upon changes in the refractive index of the mobile phase traveling through the photonic crystal column, which cause a shift in a wavelength of optical diffraction along the length of the photonic crystal that can be monitored spectroscopically.

81. The chromatographic method according to claim 80 wherein the changes in the refractive index of the mobile phase arises due to a change of the composition of the mobile phase constituents or due to the presence of dissolved chemical moieties.

82. The chromatographic method according to claim 80 wherein said photonic band structure displays a photonic band structure, which can be detected either in reflection or transmission or in combinations thereof in the ultraviolet, visible, near infrared and/or infrared spectrum of electromagnetic radiation.

83. The chromatographic method according to claim 55 wherein the photonic crystal column is produced by inverting the array of packed colloidal crystal particles within an elongated housing, wherein inversion is achieved by infiltrating a material of pre-selected index of refraction and surface properties into the interconnected voids and the colloidal crystal particles are removed thereby leaving behind an array of interconnected air-voids, which in combination with the material of pre-selected index of refraction, forms a second photonic crystal column and flow passageways through said material of pre-selected index of refraction and surface properties for a liquid, gaseous, critical, or supercritical mobile phase containing materials to be separated by the second photonic crystal column.

84. The chromatographic method according to claim 83 wherein the second colloidal photonic crystal column is removed from the elongated housing to form a free-standing colloidal photonic crystal column.

85. The chromatographic method according to claim 83 wherein the second colloidal photonic crystal column includes a solid comprising a gradient of several constituents along the length of the second photonic crystal column, wherein the array of interconnected air-voids forms flow passageways through said graduated materials of pre-selected index of refraction and surface properties for a liquid, gaseous, critical, or supercritical mobile phase containing materials to be separated by the material gradient photonic crystal column.

86. The chromatographic method according to claim 85 wherein the second colloidal photonic crystal column is removed from the elongated housing to form a free-standing second colloidal photonic crystal column.

87. The chromatographic method according to claim 83 wherein the second colloidal photonic crystal column comprises a gradient of surface-modifying reagent constituents along a length of the second photonic crystal column, and wherein the array of interconnected air-voids forms flow passageways through said material of pre-selected index of refraction having the gradient of surface-modifying reagent constituents for a liquid, gaseous, critical, or supercritical mobile phase containing materials to be separated by the surface modified photonic crystal column.

88. The chromatographic method according to claim 87 wherein the second colloidal photonic crystal column is removed from the elongated housing to form a free-standing second colloidal photonic crystal column.

89. The chromatographic method according to claim 83 wherein the second colloidal photonic crystal column includes a solid comprising a gradient of several constituents along a length of the second photonic crystal column, and including a gradient of surface-modifying reagent components along the length of the second photonic crystal, and wherein the array of interconnected air-voids forms flow passageways through said material of pre-selected index of refraction and graduated surface properties for a liquid, gaseous, critical, or supercritical mobile phase containing materials to be separated by the surface gradient modified and material gradient photonic crystal column.

90. The chromatographic method according to claim 89 wherein the second colloidal photonic crystal column is removed from the elongated housing to form a free-standing second colloidal photonic crystal column.

91. The chromatographic method according to claim 83 wherein the interconnected air-voids are substantially monodisperse.

92. The chromatographic method according to claim 83 wherein the substantially monodisperse air-voids have diameters in a range from about 50 nanometers to about 3 micrometers.

93. The chromatographic method according to claim 83 wherein said material of pre-selected index of refraction is selected from the group consisting of ceramics, silica, titania, zirconia, alumina, magnesia, oxides, chalcogenides, borides, carbides, pnictides, silicides, metals, polymers, nano-crystals, composites of aforesaid materials.

94. The chromatographic method according to claim 93 wherein said polymers are selected from the group consisting of cross-linked and non-cross-linked polystyrene, polymethacrylate, polyacrylate, polyurethane, polyketone, polyether, polyvinyl, polybutadiene, inorganic polymers, metallopolymers, copolymers, grafted polymers, block-copolymers, dendrimers, biopolymers, and composites of aforesaid polymer materials.

95. The chromatographic method according to claim 83 wherein said material of pre-selected index of refraction and surface properties is porous with different pore sizes in a range from Ångstroms to an order of micrometers.

96. The chromatographic method according to claim 83 wherein said material of pre-selected index of refraction is porous having ordered monodisperse pores with pore sizes in a range from Ångstroms to an order of micrometers.

97. The chromatographic method according to claim 83 wherein said material of pre-selected index of refraction is a solid or gel.

98. The chromatographic method according to claim 83 wherein an interior surface of said material of pre-selected index of refraction, in which the air-voids are embedded, is modified by one of plasma treatment in the presence of reactive or non-reactive gases, by chemical agents including physically or chemically surface-immobilizing said agents selected from the group consisting of etching agents, hydrophobic agents, charge-altering and carrying agents, functional group carrying agents, surface-active molecules, biomolecular agents, nanoclusters and polyelectrolytes.

99. The chromatographic method according to claim 83 wherein the colloidal photonic crystal column has a length in a range from micrometers to meters.

100. The chromatographic method according to claim 83 wherein the elongated housing is made of a material which is optically transparent or partially transparent material in the ultra-violet, visible, near infrared and infrared spectral regions.

101. The chromatographic method according to claim 100 wherein the elongated housing is rigid or flexible.

102. The chromatographic method according to claim 100 wherein the elongated housing has an inner cross-section which is one of square, rectangular, triangular, hexagonal, elliptical and circular, and wherein the inner cross-section has dimensions in a range from about 10 micrometers to several centimeters.

103. The chromatographic method according to claim 100 wherein the elongated housing is porous.

104. The chromatographic method according to claim 103 wherein said porous elongated housing has pores with different pore sizes in a range from Ångstroms to an order of micrometers.

105. The chromatographic method according to claim 103 wherein said porous elongated housing has ordered monodisperse pores with pore sizes in a range from Ångstroms to an order of micrometers.

106. The chromatographic method according to claim 100 wherein the elongated housing includes chemical surface patterns on the interior surface of the elongated housing.

107. The chromatographic method according to claim 100 wherein the elongated housing includes relief surface patterns on the interior surface of the elongated housing.

108. The chromatographic method according to claim 100 wherein the elongated housing is made of a material selected from the group consisting of polymers, oxides, chalcogenides, glasses, metals and semiconductors, combinations and composites of aforesaid materials.

109. The chromatographic method according to claim 83 wherein the step of spectroscopically monitoring for changes in the photonic band structure of the photonic crystal column includes coupling an optical system to said photonic crystal column for monitoring changes in the photonic band structure of the photonic crystal column, wherein said optical system includes a light source, directing and focusing optics for guiding a beam of light from said light source to said photonic crystal column and from said photonic crystal column in reflectance or transmission mode to a light analysis means for spectrally dispersing the light after interaction of the light beam with the photonic crystal column, and detection means for detecting said dispersed light.

110. The chromatographic method according to claim 83 including moving the optical system along a length of said photonic crystal column.

111. The chromatographic method according to claim 83 wherein said changes in the photonic band structure of the photonic crystal column as a liquid, gaseous, critical, or supercritical mobile phase containing materials to be separated is flowed through said photonic crystal column and separated therein include changes in the photonic band structure upon changes in the refractive index of the mobile phase traveling through the photonic crystal column, which cause a shift in a wavelength of optical diffraction along the length of the photonic crystal that can be monitored spectroscopically.

112. The chromatographic method according to claim 83 wherein the changes in the refractive index of the mobile phase arises due to a change of the composition of the mobile phase constituents or due to the presence of dissolved chemical moieties.

113. The chromatographic method according to claim 83 wherein said photonic band structure displays a photonic band structure, which can be detected either in reflection or transmission or in combinations thereof in the ultraviolet, visible, near infrared and/or infrared spectrum of electromagnetic radiation.

* * * * *